(12) United States Patent
Xavier et al.

(10) Patent No.: US 10,861,592 B2
(45) Date of Patent: Dec. 8, 2020

(54) REDUCING INFUSION PUMP NETWORK CONGESTION BY STAGGERING UPDATES

(71) Applicant: ICU Medical, Inc., San Clemente, CA (US)

(72) Inventors: Ben Xavier, San Diego, CA (US); Dennis Krabbe, San Diego, CA (US); Larry Enger, Oceanside, CA (US); Chaitanya Deosthale, San Diego, CA (US); Anthony Isensee, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/512,193

(22) Filed: Jul. 15, 2019

(65) Prior Publication Data
US 2020/0027542 A1    Jan. 23, 2020

Related U.S. Application Data

(63) Continuation of application No. PCT/US2019/041705, filed on Jul. 12, 2019.
(Continued)

(51) Int. Cl.
*G16H 20/17* (2018.01)
*A61M 5/142* (2006.01)
(Continued)

(52) U.S. Cl.
CPC ............ *G16H 20/17* (2018.01); *A61M 5/142* (2013.01); *G06F 8/65* (2013.01); *G06F 9/542* (2013.01);
(Continued)

(58) Field of Classification Search
None
See application file for complete search history.

(56) References Cited

U.S. PATENT DOCUMENTS

| 4,024,864 A | 5/1977 | Davies et al. |
| 4,055,175 A | 10/1977 | Clemens et al. |

(Continued)

FOREIGN PATENT DOCUMENTS

| CA | 2 060 151 | 8/1997 |
| CA | 2 125 300 | 10/1999 |

(Continued)

OTHER PUBLICATIONS

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.
(Continued)

*Primary Examiner* — Devin C Hein
(74) *Attorney, Agent, or Firm* — Knobbe, Martens, Olson & Bear, LLP

(57) ABSTRACT

A system can include a plurality of infusion pumps and a connectivity adapter in a clinical environment. The connectivity adapter can receive update data, such as a drug library update or an operational software update, and can store the update data within the clinical environment. The connectivity adapter can send the update data to a predetermined number of infusion pumps that have requested the update. At least two subsets of the infusion pumps can receive different blocks of the update data at about the same time. Further, the same or different update data can be provided to the infusion pumps at about the same time.

19 Claims, 15 Drawing Sheets

Related U.S. Application Data

(60) Provisional application No. 62/699,454, filed on Jul. 17, 2018.

(51) Int. Cl.
*G16H 40/67* (2018.01)
*G16H 40/63* (2018.01)
*G16H 40/20* (2018.01)
*G16H 40/40* (2018.01)
*G06F 8/65* (2018.01)
*G06F 9/54* (2006.01)
*A61M 5/172* (2006.01)

(52) U.S. Cl.
CPC ............. *G16H 40/20* (2018.01); *G16H 40/40* (2018.01); *G16H 40/63* (2018.01); *G16H 40/67* (2018.01); *A61M 5/172* (2013.01); *A61M 2005/14208* (2013.01); *A61M 2205/18* (2013.01); *A61M 2205/3561* (2013.01); *A61M 2205/3584* (2013.01); *A61M 2205/3592* (2013.01); *A61M 2205/52* (2013.01)

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |

(56) References Cited

U.S. PATENT DOCUMENTS

| | | |
|---|---|---|
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,032,155 A | 2/2000 | de la Huerga |
| 6,032,676 A | 3/2000 | Moore |
| 6,039,251 A | 3/2000 | Holowko et al. |
| 6,073,106 A | 6/2000 | Rozen et al. |
| 6,104,295 A | 8/2000 | Gaisser et al. |
| 6,112,182 A | 8/2000 | Akers et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |

(56) References Cited

U.S. PATENT DOCUMENTS

| | | |
|---|---|---|
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B2 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wermeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |

(56) References Cited

U.S. PATENT DOCUMENTS

| | | |
|---|---|---|
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | Vandanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,147,448 B2 | 4/2012 | Sundar et al. |
| 8,149,131 B2 | 4/2012 | Blornquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 * | 3/2013 | Leibner-Druska ..... G16H 20/17 604/131 |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,922,330 B2 | 12/2014 | Moberg et al. |
| 8,936,565 B2 | 1/2015 | Chawla |
| 8,952,794 B2 | 2/2015 | Bloomquist et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,381,296 B2 | 7/2016 | Arrizza et al. |
| 9,393,362 B2 | 7/2016 | Cozmi et al. |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,971,871 B2 | 5/2018 | Arrizza et al. |

(56) References Cited

U.S. PATENT DOCUMENTS

| | | |
|---|---|---|
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,430,761 B2 | 10/2019 | Hume et al. |
| 10,434,246 B2 | 10/2019 | Silkaitis et al. |
| 10,463,788 B2 | 11/2019 | Day |
| 10,617,815 B2 | 4/2020 | Day et al. |
| 10,646,651 B2 | 5/2020 | Day et al. |
| 10,692,595 B2 | 6/2020 | Xavier et al. |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0173702 A1 | 11/2002 | Lebel et al. |
| 2002/0173875 A1 | 11/2002 | Wallace et al. |
| 2002/0194329 A1 | 12/2002 | Ailing |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 * | 11/2003 | Gillies .................... H04L 45/02 709/238 |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0117529 A1 | 6/2005 | Ramos-Escano |
| 2005/0119788 A1 | 6/2005 | Engleson et al. |

(56) References Cited

U.S. PATENT DOCUMENTS

| | | |
|---|---|---|
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1* | 2/2008 | Wahl ............... H04L 29/12132 |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |

(56) References Cited

U.S. PATENT DOCUMENTS

| | | |
|---|---|---|
| 2008/0320387 A1 | 12/2008 | Sasaki et al. |
| 2008/0320466 A1 | 12/2008 | Dias |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150878 A1* | 6/2009 | Pathak ............... G06F 8/65 717/172 |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0175728 A1 | 7/2011 | Baker, Jr. |
| 2011/0178462 A1 | 7/2011 | Moberg et al. |
| 2011/0196748 A1 | 8/2011 | Caron et al. |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012877 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1* | 2/2013 | Birtwhistle ............... G06F 8/65 717/171 |
| 2013/0066265 A1 | 3/2013 | Grant |
| 2013/0072872 A1 | 3/2013 | Yodfat et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0104120 A1* | 4/2013 | Arrizza ............... G06F 8/65 717/173 |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0167245 A1 | 6/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1* | 1/2014 | Chandrasenan .... G06F 19/3481 705/2 |
| 2014/0039446 A1 | 2/2014 | Day |
| 2014/0163517 A1 | 6/2014 | Finan et al. |

(56) References Cited

U.S. PATENT DOCUMENTS

| | | | |
|---|---|---|---|
| 2014/0180711 A1 | 6/2014 | Kamen et al. | |
| 2014/0254598 A1* | 9/2014 | Jha | G16H 40/67 370/392 |
| 2014/0257251 A1 | 9/2014 | Bush et al. | |
| 2014/0266790 A1 | 9/2014 | Al-Ali et al. | |
| 2014/0269643 A1 | 9/2014 | Sun | |
| 2014/0276571 A1* | 9/2014 | Ludolph | G06F 19/3468 604/506 |
| 2014/0288947 A1 | 9/2014 | Simpson et al. | |
| 2014/0297329 A1 | 10/2014 | Rock | |
| 2014/0366878 A1 | 12/2014 | Baron | |
| 2015/0005935 A1 | 1/2015 | Bae et al. | |
| 2015/0066531 A1 | 3/2015 | Jacobson et al. | |
| 2015/0100038 A1 | 4/2015 | McCann et al. | |
| 2015/0151051 A1 | 6/2015 | Tsoukalis | |
| 2015/0161354 A1 | 6/2015 | Blomquist | |
| 2015/0199192 A1* | 7/2015 | Borges | G16H 20/17 717/172 |
| 2015/0230760 A1* | 8/2015 | Schneider | G06F 19/3468 600/300 |
| 2015/0328396 A1* | 11/2015 | Adams | G06F 3/04847 604/500 |
| 2015/0371004 A1* | 12/2015 | Jones | G06F 19/326 705/2 |
| 2015/0379237 A1 | 12/2015 | Mills et al. | |
| 2016/0015885 A1 | 1/2016 | Pananen et al. | |
| 2016/0034655 A1* | 2/2016 | Gray | G16H 70/40 713/1 |
| 2016/0045661 A1 | 2/2016 | Gray et al. | |
| 2016/0051749 A1 | 2/2016 | Istoc | |
| 2016/0051751 A1 | 2/2016 | Silkaitis et al. | |
| 2016/0103960 A1 | 4/2016 | Hume et al. | |
| 2016/0228633 A1 | 8/2016 | Welsch et al. | |
| 2016/0241391 A1 | 8/2016 | Fenster | |
| 2016/0350513 A1 | 12/2016 | Jacobson et al. | |
| 2017/0262590 A1 | 9/2017 | Karakosta et al. | |
| 2017/0274140 A1 | 9/2017 | Howard et al. | |
| 2017/0286637 A1 | 10/2017 | Arrizza et al. | |
| 2017/0319780 A1 | 11/2017 | Belkin et al. | |
| 2018/0121613 A1 | 5/2018 | Connely, IV et al. | |
| 2018/0181712 A1 | 6/2018 | Ensey et al. | |
| 2018/0247712 A1 | 8/2018 | Muhsin et al. | |
| 2019/0006044 A1* | 1/2019 | Brask | G16H 40/40 |
| 2019/0096518 A1 | 3/2019 | Pace | |
| 2019/0147998 A1 | 5/2019 | Ruchti et al. | |
| 2019/0228863 A1 | 7/2019 | Dharwad et al. | |
| 2019/0240405 A1 | 8/2019 | Wehba et al. | |
| 2019/0243829 A1 | 8/2019 | Butler et al. | |
| 2019/0269852 A1 | 9/2019 | Kohlbrecher | |
| 2019/0311803 A1 | 10/2019 | Kohlbrecher et al. | |
| 2020/0027541 A1 | 1/2020 | Xavier et al. | |
| 2020/0027543 A1 | 1/2020 | Xavier et al. | |
| 2020/0027548 A1 | 1/2020 | Xavier et al. | |
| 2020/0027549 A1 | 1/2020 | Xavier et al. | |
| 2020/0027550 A1 | 1/2020 | Xavier et al. | |
| 2020/0027551 A1 | 1/2020 | Xavier et al. | |
| 2020/0028837 A1 | 1/2020 | Xavier et al. | |
| 2020/0028914 A1 | 1/2020 | Xavier et al. | |
| 2020/0028929 A1 | 1/2020 | Xavier et al. | |
| 2020/0035355 A1 | 1/2020 | Xavier et al. | |
| 2020/0061291 A1 | 2/2020 | Day et al. | |
| 2020/0145332 A1 | 5/2020 | Jha et al. | |
| 2020/0206413 A1 | 7/2020 | Silkaitis et al. | |

FOREIGN PATENT DOCUMENTS

| | | |
|---|---|---|
| CA | 2 898 825 | 7/2014 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |

(56) References Cited

FOREIGN PATENT DOCUMENTS

| | | |
|---|---|---|
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/124569 | 8/2015 |
| WO | WO 2019/219290 | 11/2019 |

OTHER PUBLICATIONS

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. http://corp.bbraun.ee/Extranet/Infusioonjpumbad/Kasutusjuhendid/Vanad/Kasutusjuhend-Infusomat_Space(vers688J.inglise_K).pdf.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.

"CareAware® Infusion Management", Cerner Store, as printed May 12, 2011, pp. 3, https://store.cerner.com/items/7.

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing13 Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

East PhD et al., "Digital Electronic Communication Between ICU Ventilators and Computers and Printers", Respiratory Care, Sep. 1992, vol. 37, No. 9, pp. 1113-1122.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification" Wikipedia.org dated Oct. 11 2011 in 2 pages, https://en.wikipedia.org/w/index.php?title=File_verification&oldid=455048290.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D. et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

(56) References Cited

OTHER PUBLICATIONS

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-12.
Introducing Abbott TQPM (Total Quality Pain Management), Abbott Laboratories, Abbott Park, IL, May 2000, pp. 1-4.
"Infusion Pump", Wikipedia.org, https://web.archive.org/web/20140703024932/https://en.wikipedia.org/wiki/infusion_pump, as last modified Mar. 27, 2014, pp. 3.
International Search Report and Written Opinion received in PCT Application No. PCT Application No. PCT/US2019/041705, dated Sep. 17, 2019 in 37 pages.
Invitation to Pay Additional Fees received in PCT Application No. PCT/US2019/041705, dated Aug. 7, 2019 in 2 pages.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version v1.1, Sep. 2011, pp. 154. http://www.medfusionpump.com/assets/literature/manuals/Operators_Manual_4000_40-5760-51A.pdf.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Micrel Medical Devices, "MP Daily +" http://web.archive.org/web/20130803235715/http://www.micrelmed.com/index.aspx?productid=9 as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, http://incenter.medical.phillips.com/doclib/enc/fetch/2000/4504/577242/577243/577247/5826646/583147/8359175/Philips_Patient_Monitoring_and_IntelliSpace_Even_Management_Interoperability.pdf%3fnodeid%3d8508574%26vemum%3d-2, pp. 2.
Pretty et al., "Hypoglycemia Detection in Critical Care Using Continuous Glucose Monitors: an in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

(56) References Cited

OTHER PUBLICATIONS

Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpl4209-832.pdf.
Slack, W.V., "Information Technologies for Transforming Health Care", https://www.andrew.cmu.edu/course/90-853/medis.dir/otadocs.dir./03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "A Center Keeps Medicine in Right Hands", The Capital Journal, Dec. 4, 1999, pp. 1-2.
"Software Versioning", Wikipedia.org, dated Oct. 16, 2011 in 11 pages. https://en.wikipedia.org/w/index.php?title=Software_versioning&oldid=455859110.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
"Context-Free Grammar", Wikipedia.org, as last modified Mar. 5, 2010 in 11 pages, https://en.wikipedia.org/w/index.php/?title=Context-free_grammar&oldid=347915989.

\* cited by examiner

Device List

Update Selected Devices: Software　　　　Select a Device Type　　　　　　　　　　　　⊕ Update All　⊕ Update Selected

| Select a Device Type<br>✓ Selected | [Plum 360]<br>✓ Selected |
|---|---|

Select a Software Version
✗ Incomplete

Select a Facility
✓ Selected

Schedule a Start Time
✓ Selected

Update Summary

Device Type:　　Plum 360
Facility:　　43De2c3e-b2c6-437D-895f-191c54926a60
Software Version:
Start Time:　　Mon Jul 02 2018 13:39:15 GMT-0700 (Pacific Daylight Time)
Total Devices in this Update:　　1

Displaying: 1 of 4 Devices | No Filters Applied　(Add/Edit a Filter +)　　　　　　　　　　　　　　　　　　　　　　(SHARED RESET)

| ☐ | Device Name ⊕ | Device Type | Operational Status ⊕ | Library Version ⊕ | Software Version | Drug Library Update Status ⊕ | Software Update Status ⊕ | Facility ⊕ | Update Status | Current Alarms ⊕ | Network Status | Power Status ⊕ |
|---|---|---|---|---|---|---|---|---|---|---|---|---|
| ☑ | HSPRO1014CD414000 3B144ACA501 | Plum 360 | Idling | 000000000000000000000000000000 | 03.04.00.159 | Download Complete | Update Status Not Found | 43De2c3e-b2c6-4370-895f-191c54926a60 | | Valve Cassette Test Failed Cleared | 🛜 | 🔋 |

Date Last Updated: 7/2/2018, 1:39:05 PM | ⟳ Refreshing every 30 seconds

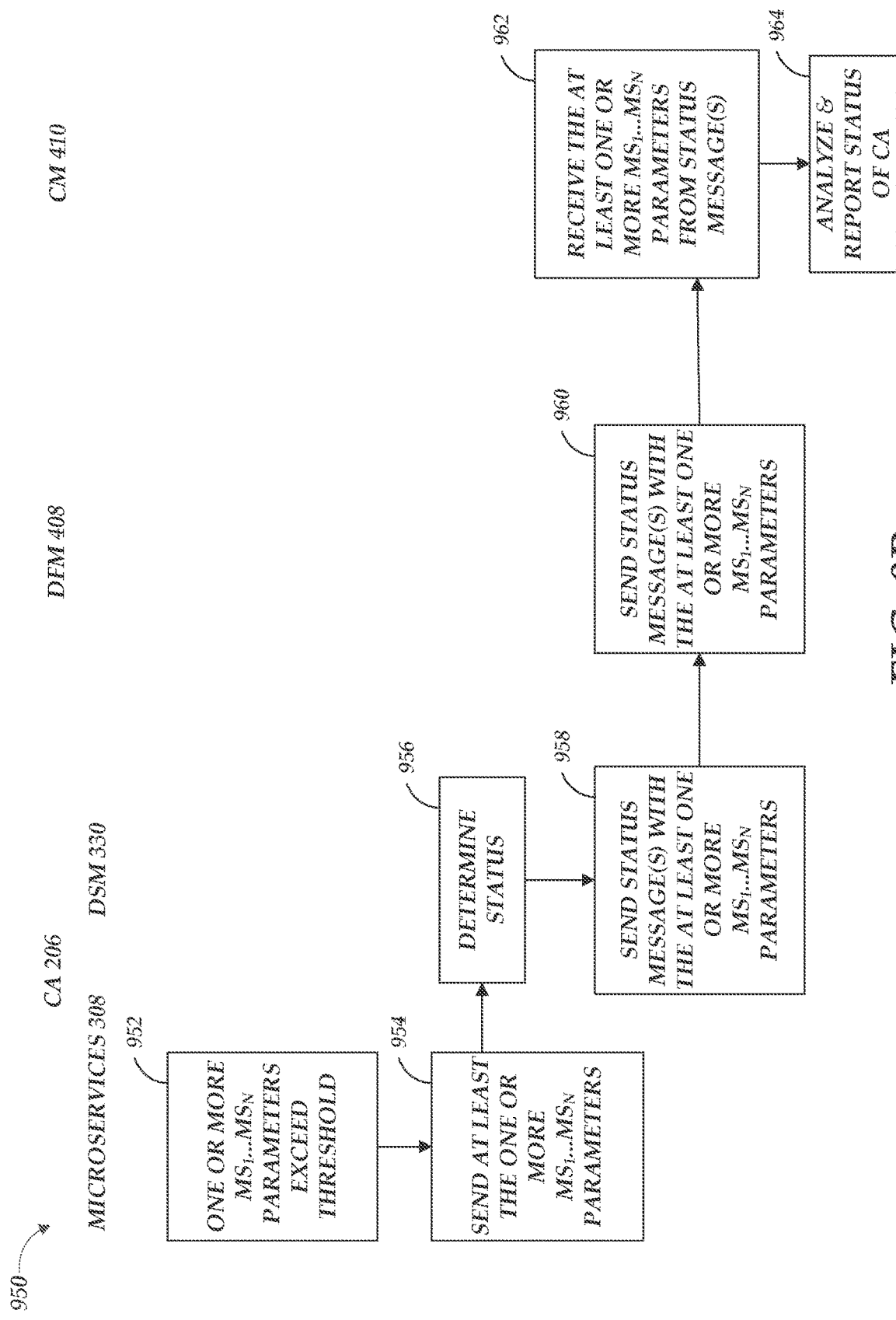

REDUCING INFUSION PUMP NETWORK CONGESTION BY STAGGERING UPDATES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

This disclosure relates to the field of clinical messaging, and particularly to techniques for facilitating clinical messaging within and across various network environments.

BACKGROUND

Modern medical care often involves the use of medical infusion pumps to deliver fluids and/or fluid medicine to patients. Infusion pumps permit the controlled delivery of fluids to a patient and provide flexible yet controlled delivery schedules. Drug libraries within the infusion pumps provide some limits pertaining to the delivery of fluids. Infusion pumps can communicate with a server configured to manage drug library updates and operational software updates of the individual infusion pumps.

SUMMARY

Various techniques for facilitating communication with and across a clinical environment and a cloud environment are described herein. These techniques may include converting pump messages into standardized dataset messages (also referred to herein simply as "messages"), updating drug libraries, updating pump operational software, detecting health status parameters, sending health status parameters, among others. These and other embodiments are described in greater detail below with reference to FIGS. 1-9B. Although many of the examples are described in the context of a hospital environment including infusion pumps, the techniques described herein can be applied to any network environment including other medical devices (e.g., patient care monitors configured to display blood pressure, heart rate, blood oxygenation, and the like), or non-medical devices, or any combination thereof.

A distributed system can include a server outside of a clinical environment and a connectivity adapter and a plurality of infusion pumps within the clinical environment. The connectivity adapter can receive from the server a location of an update, such as a drug library update or an operational software update, to be delivered to the infusion pumps. The location can be received over a first messaging communication channel of a network, and the update data can be received over a second, data communication channel of the network. The update data can be stored at the connectivity adapter such that it can be sent to the infusion pumps.

A system can include a plurality of infusion pumps and a connectivity adapter in a clinical environment. The connectivity adapter can receive update data, such as a drug library update or an operational software update, and can store the update data within the clinical environment. The connectivity adapter can send the update data to a predetermined number of infusion pumps that have requested the update. At least two subsets of the infusion pumps can receive different blocks of the update data at about the same time. Further, the same or different update data can be provided to the infusion pumps at about the same time.

A distributed system can include a server outside of a clinical environment and a connectivity adapter and a plurality of infusion pumps within the clinical environment. The connectivity adapter can monitor microservices that measure the quality of connectivity adapter's performance. If the performance is below a threshold level, a message indicating poor performance can be sent to the server. The message can be sent when a prior message relating to poor performance has not already been sent within a predetermined time period.

BRIEF DESCRIPTION OF THE DRAWINGS

The embodiments described herein are illustrated by way of example, and not by way of limitation, in the figures of the accompanying drawings in which like references indicate similar elements.

FIG. 6A illustrates an example user interface for scheduling a software update.

FIG. 9B is a block diagram illustrating an example self-reporting system to provide the status of connectivity adapters.

DETAILED DESCRIPTION

Overview of Example Network Environment

Figure 1:
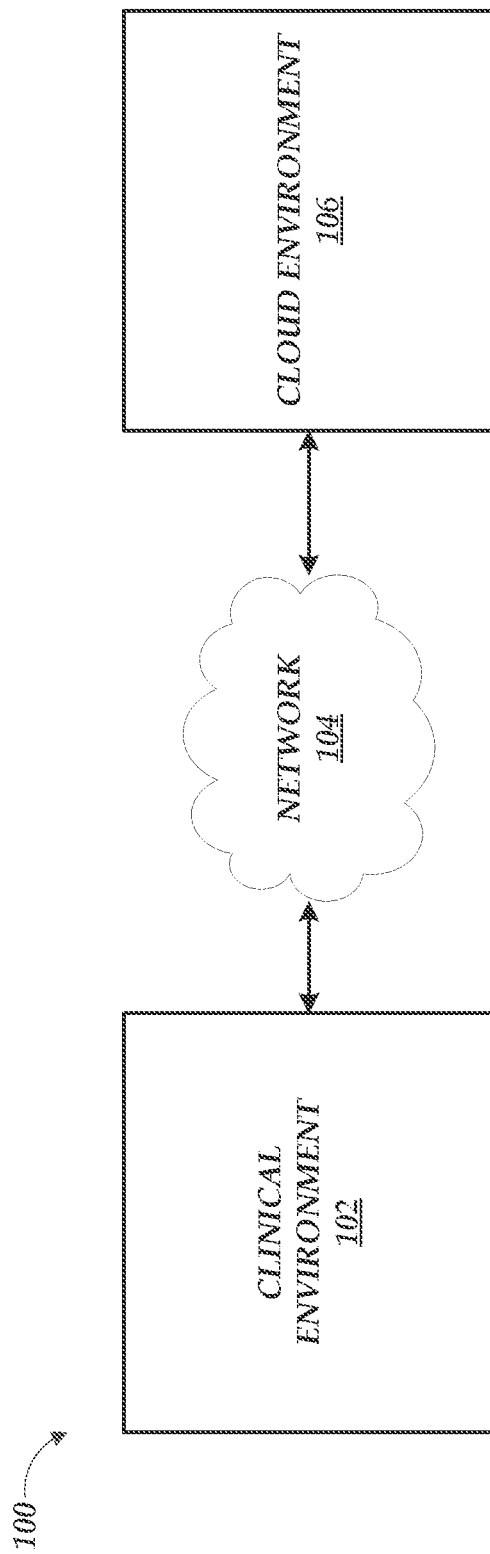
FIG. 1 is a block diagram of an example clinical environment and an example cloud environment.

FIG. 1 illustrates an example network environment 100 in which clinical environment 102 communicates with cloud environment 106 via network 104. The clinical environment 102 may include one or more healthcare facilities (e.g., hospitals). The components of the clinical environment 102 are described in greater detail below with reference to FIG. 2. The network 104 may be any wired network, wireless network, or combination thereof. In addition, the network 104 may be a personal area network, local area network, wide area network, over-the-air broadcast network (e.g., for radio or television), cable network, satellite network, cellular telephone network, or combination thereof. For example, the network 104 may be a publicly accessible network of linked networks such as the Internet. Protocols and components for communicating via the Internet or any of the other aforementioned types of communication networks are well known to those skilled in the art and, thus, are not described in more detail herein. For example, the clinical environment 102 and the cloud environment 106 may each be implemented on one or more wired and/or wireless private networks, and the network 104 may be a public network (e.g., the Internet) via which the clinical environment 102 and the cloud environment 106 communicate with each other. The cloud environment 106 may be a cloud-based platform configured to communicate with multiple clinical environments. The cloud environment 106 may include a collection of services, which are delivered via the network 104 as web services. The components of the cloud environment 106 are described in greater detail below with reference to FIG. 4.

Components of Clinical Environment

Figure 2:
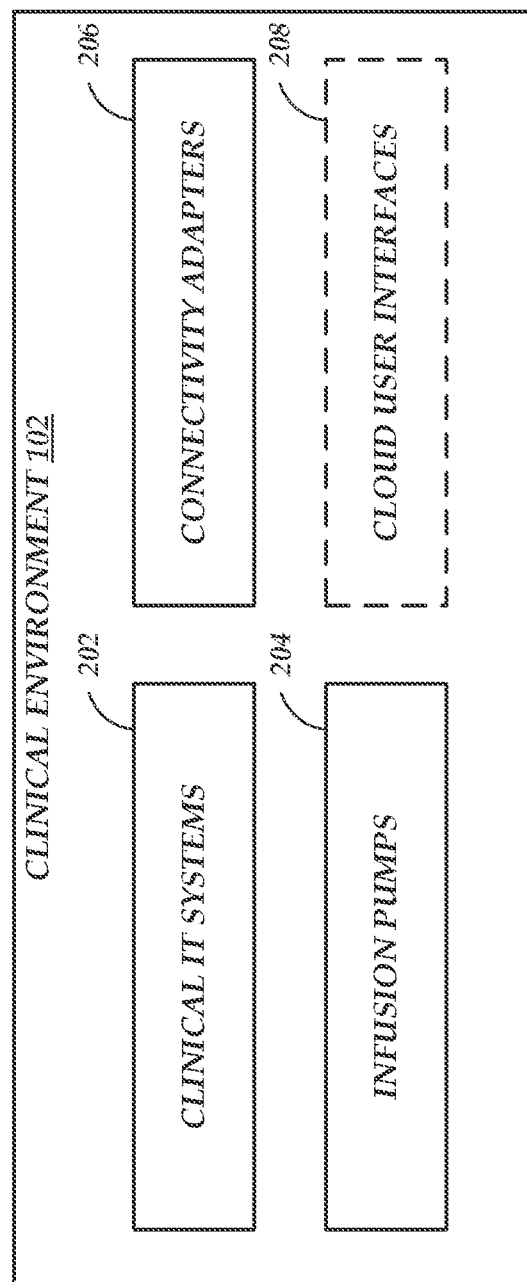
FIG. 2 is a block diagram illustrating example components of a clinical environment.

FIG. 2 illustrates the clinical environment 102, which includes one or more clinical IT systems 202, one or more infusion pumps 204, and one or more connectivity adapters 206. Further, the clinical environment 102 may be configured to provide cloud user interfaces 208 (e.g., generated and provided by the cloud environment 106). The clinical IT system 202 may include a hospital information system (HIS) designed to manage the facilities' operation, such as medical, administrative, financial, and legal issues and the corresponding processing of services. The infusion pump 204 is a medical device configured to deliver medication to a patient. The connectivity adapter 206 is a network component configured to communicate with other components of the clinical environment 102 and also communicate with the cloud environment 106 on behalf of the other components of the clinical environment 102. In some cases, the connectivity adapter 206 is a network appliance with limited storage space (e.g., memory and/or persistent storage). The cloud user interfaces 208 may be provided to a user in the clinical environment 102 via a browser application, desktop application, mobile application, and the like. The user may access status reports and other data stored in the cloud environment 106 via the cloud user interfaces 208.

The components 202-208 illustrated in FIG. 2 may communicate with one or more of the other components in the clinical environment 102. For example, each of the clinical IT system 202 and the infusion pump 204 may communicate with the connectivity adapter 206 via physical local area network (LAN) and/or virtual LAN (VLAN). The components 202-208 may communicate messages in the clinical environment 102 over a message channel of the local network and may communicate data in the clinical environment 102 over a data channel of the local network. Although not shown in FIG. 2, the clinical environment 102 may include other medical devices and non-medical devices that facilitate the operation of the clinical environment 102.

Overview of Messaging in the Clinical Environment

Figure 3:
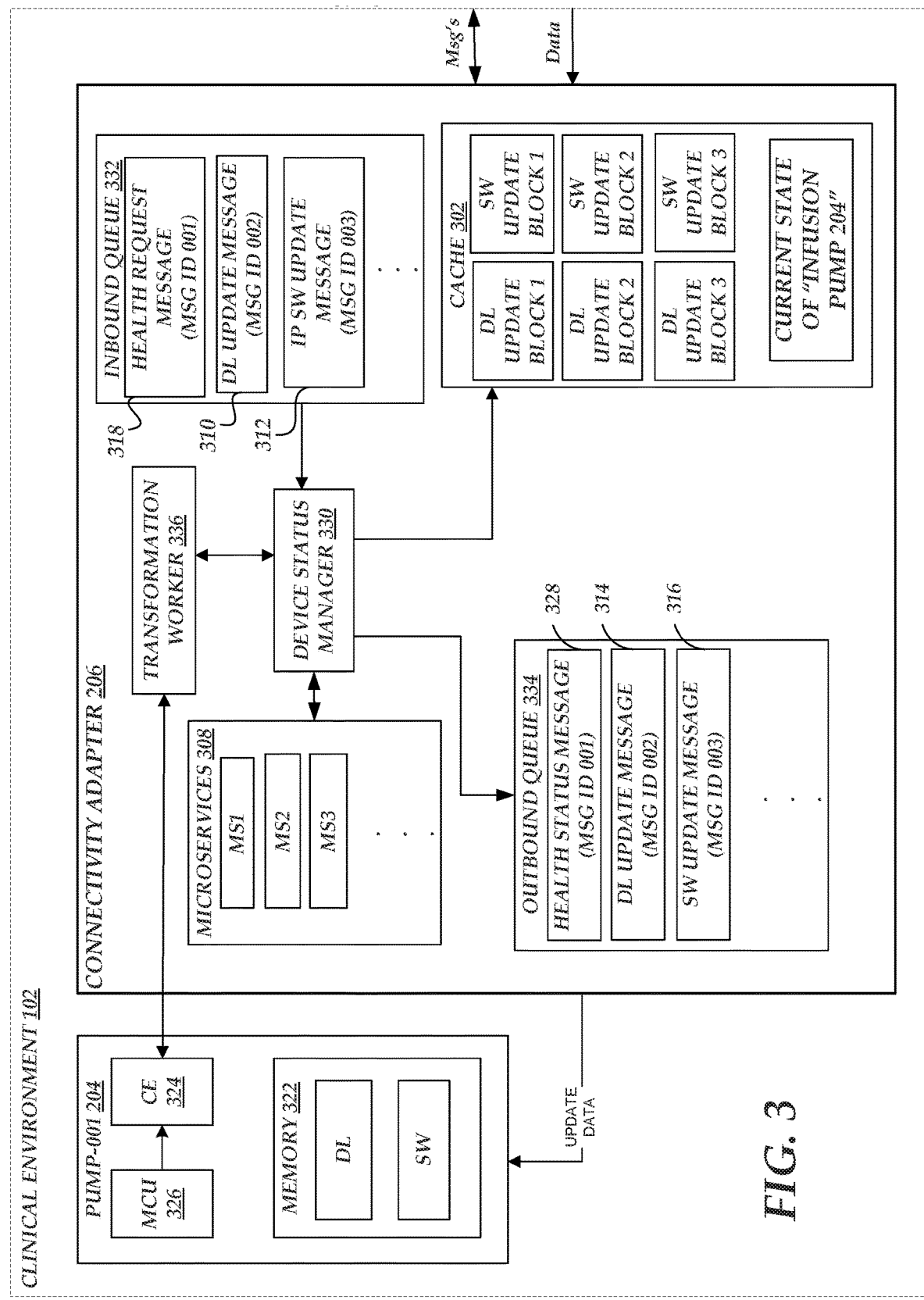
FIG. 3 is a schematic diagram illustrating example components of an infusion pump and a connectivity adapter of a clinical environment.

FIG. 3 illustrates example messages and data received, stored, and transmitted by the connectivity adapter 206 in the clinical environment 102. As shown in FIG. 3, the infusion pump 204 may include motor controller unit (MCU) 326 and communications engine (CE) 324, and memory 332 storing at least one or more drug libraries and operational software. The drug libraries include boundaries for drug delivery for various medications that can be delivered to patients by infusion pumps. The operational software can include the operating system of the infusion pump, as well as other software for performing various functions. Each type of infusion pump and even different versions of the same type of infusion pump may operate with a different operating system. The MCU 326 can use a less powerful processor (e.g., 12 MHz) and the CE 324 can use a more powerful processor (e.g., 400 MHz).

The MCU 326 may generate and send pump messages to the CE 324 for storage and transmission to the connectivity adapter 206. In some cases, the messages are each associated with a message ID. A message ID can be a unique identifier or a sequence identifier. The pump messages may include clinical information. The CE 324 may send such pump messages to the connectivity adapter 206. Pump messages sent to the connectivity adapter 206 via the CE 324 and generated by the MCU 326 may be transformed by the transformation worker 336 into a standardized dataset message (e.g., message format used by the connectivity adapter 206 to communicate with the cloud environment 106, sometimes referred herein as simply a message).

The CE 324 may also receive messages from the connectivity adapter 206 indicating that updates, such as updates to the drug library or updates to the operational software are available and may send messages to the connectivity adapter 206 requesting the updates (e.g., update data). The CE 324 may also receive the update data from the connectivity adapter 206 for storage in the memory 322. The update data may be drug library update data or may be operational software update data. The operational software update may include one or more of a device configuration, a network configuration, certificate(s), language pack(s), software update images, software update patches, security updates, and the like. The update data may be provided over a different communication channel than the communication channel(s) used to send or receive messages.

As also shown in FIG. 3, the connectivity adapter 206 may include transformation worker 336, device status manager 330, cache 302, inbound queue 332, outbound queue 334, and microservices 308. The transformation worker 336 may transform the messages sent to the connectivity adapter 206 from the infusion pump 204 into the standardized dataset message. The transformation worker 336 may also transform messages sent from the connectivity adapter 206 to the infusion pump 204 into a message format usable by the infusion pump 204.

The microservices 308 include one or more programs (e.g., MS1, MS2, MS3 . . . ) that perform specific service functions within the operation of the connectivity adapter 206. For example, a microservice 308 may send the message to the outbound queue 334, while another microservice 308 may receive messages and place them into the inbound queue 332. In addition to performing service functions, one or more microservices 308 may monitor the characteristics of the service functions. For example, the microservice 308 may monitor parameters related to the execution of a service function, such as, for example, the size of a queue 332, 334 or other queue, latency, memory usage, CPU time, and the like. The connectivity adapter 206 may provide the parameters to the cloud environment 106 when one or more parameters exceed a threshold, or the connectivity adapter 206 may provide the parameters upon request from the cloud environment 106.

The inbound queue 332 receives and stores messages from the cloud environment 106 for processing by the connectivity adapter 206. For example, the inbound queue 332 may receive one or more of a health request message 326, a drug library update message 310, and an infusion pump software update message from the cloud environment 106. The health request message 326 may be a request for the health or the status of the connectivity adapter 206. The drug library update message 310 may be notification that a drug library update is available for a least a portion of the infusion pumps 204 associated with the connectivity adapter 206. An infusion pump software update message 312 may be a notification that an update to the operational software for at least a portion of the infusion pumps 204 associated with the connectivity adapter 206 is available. The connectivity adapter 206 may comprise more than one inbound queue such that, for example, there is at least an inbound queue 332 for messages received from the cloud environment 106 over the network 104 and at least another inbound queue for messages received from one or more infusion pumps 204 over the local network. The messages stored in the inbound queue 332 may be associated with one or more message identifiers (IDs). A message ID can be a unique identifier or a sequence identifier. The messages received from the cloud environment 106 may be sent over a message channel associated with the network 104.

The outbound queue 334 receives and stores messages to be sent from the connectivity adapter 206. For example, the outbound queue 334 may receive a health status message 328 to be sent to the cloud environment 106 over the network 104. The outbound queue 334 may also receive a drug library update message 314 and a software update message 316 to be sent to one more infusion pumps over the local network. The health status message 328 may be a message indicating the health of the connectivity adapter 206 and may include one or more parameters from the microservices 308. The drug library update message 314 may be a notification to one or more infusion pumps 204 that a drug library update is available. The software update message 316 may be a notification to one or more infusion pumps 204 that an update to the operational software is available. The connectivity adapter 206 may comprise more than one outbound queue such that, for example, there is at least an outbound queue 334 for messages to be sent to the cloud environment 106 over the network 104 and at least another outbound queue for messages to be sent to one or more infusion pumps 204 over the local network. The messages stored in the outbound queue 334 may be associated with one or more message identifiers (IDs). A message identifier can be a unique identifier or a sequence identifier. The messages sent from the connectivity adapter 206 to the infusion pumps 204 may be sent over a message channel associated with the local network.

The device status manager 330 receives the drug library and operational software updates from the cloud environment 106 and caches blocks of the update data in the cache 302. The device status manager 330 processes the received messages from the inbound queue 332 and sends messages to the outbound queue 334 for transmission to the cloud environment 106 or to the infusion pumps 204. The data received from the cloud environment 106 may be sent over a data channel associated with the network 104 and separate from the message channel of the network 104. Because the data channel in the cloud environment is separate from the message channel in the cloud environment, the data transfer does not interfere with the clinical messaging from the connectivity adapter to the cloud environment. The data sent from the cache 302 to the infusion pumps 204 may be sent over a data channel associated with the local network and separate from the message channel associated with the local network. Because the data channel in the local network is separate from the message channel in the local network, the data transfer does not interfere with the clinical messaging from infusion pumps to the connectivity adapter. Thus, congestion on both the message channel of the cloud environment and the message channel of the local network is reduced.

The device status manager 330 also processes transformed messages provided by the transformation worker 336 and merges the data included in the transformed messages into the cache 302 to update the current state of the infusion pump 204 stored in the cache 302. Additional details regarding the messaging in the clinical environment 102 are provided below.

Components of Cloud Environment

Figure 4:
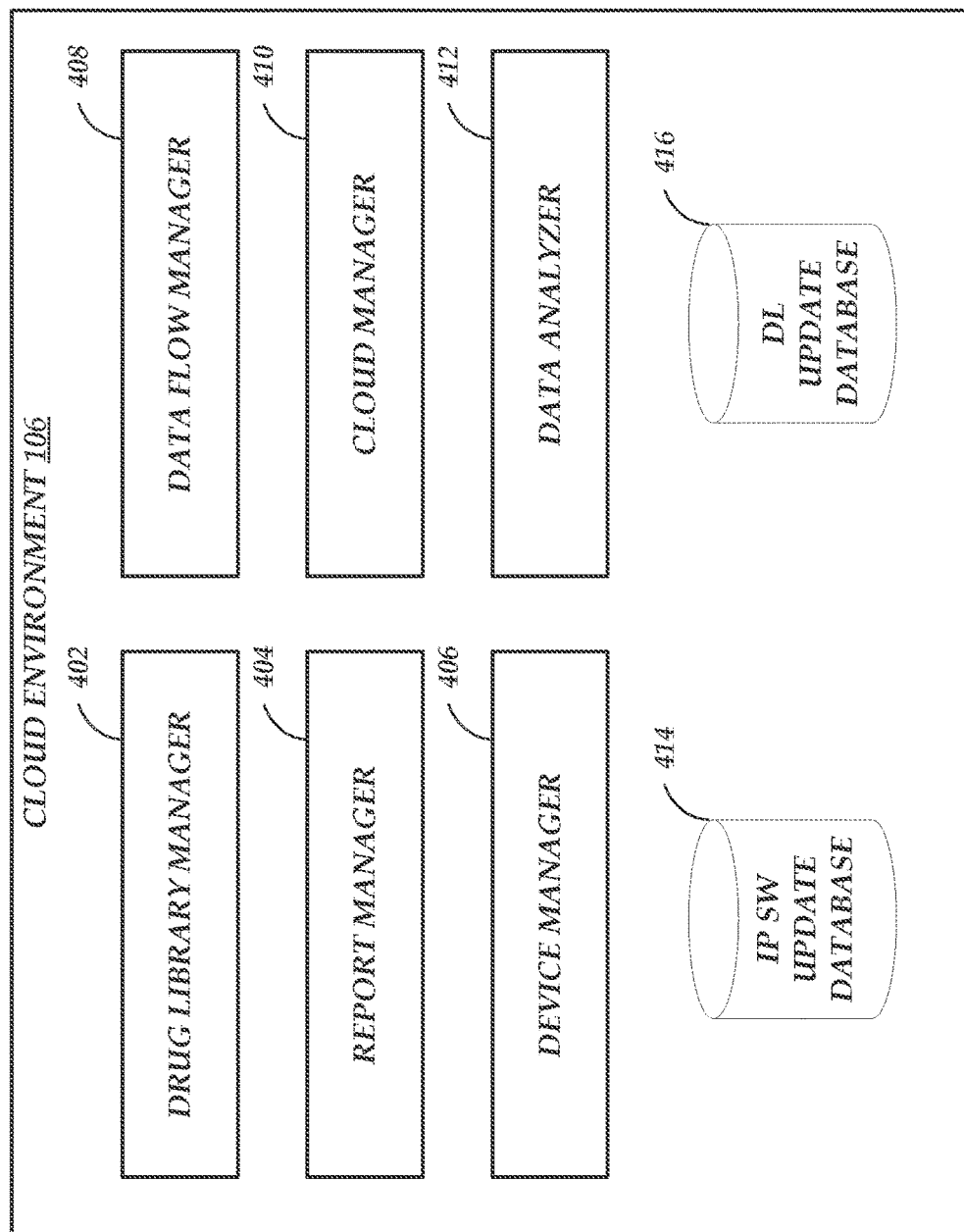
FIG. 4 is a block diagram illustrating example components of a cloud environment.

FIG. 4 illustrates an example of the cloud environment 106, which includes drug library manager (DLM) 402, report manager 404, device manager 406, data flow manager (DFM) 408, cloud manager (CM) 410, data analyzer (DA) 412, infusion pump (IP) software (SW) update database 414 and drug library update database 416.

The DLM 402 may provide a set of features and functions involved in the creation and management of drug libraries for use with infusion pumps. These drug libraries may provide user-defined settings for pump configuration and drug error reduction (DERS).

The report manager 404 may provide various reporting capabilities for clinically relevant infusion data which users can choose to use for further analysis, such as tracking and trending of clinical practices.

The device manager 406 may oversee and manage the maintenance of infusion pumps, providing users the capability to view and manage asset and operational data. For example, the device manager 406 may schedule drug library and software updates for infusion pumps.

The DFM 408 may facilitate storing, caching, and routing of data between compatible infusion pumps, Navajo software, and compatible external systems. For example, the DFM may store infusion and operational data received from infusion pumps, store and cache infusion pump drug libraries and software images, convert and route network messaging between the cloud environment 106 and the clinical environment 102, convert and route medication order information from a hospital information system to an infusion pump (e.g., auto-programming or smart-pump programming), and/or convert and route alert information and infusion events from infusion pumps to hospital information systems (e.g., alarm/alert forwarding, and auto-documentation, or infusion documentation).

The CM 410 may serve as a general-purpose computing platform for the other modules illustrated in FIG. 4. Functionally, the CM 410 may be similar to Microsoft Windows or Linux operating systems as it provides the following services: networking, computation, user administration and security, storage, and monitoring.

The DA 412 may provide data analytics tools for generating user interfaces and reports based on the data generated and/or received by the other modules illustrated in FIG. 4.

Operational software update database 414 may store operational software and/or updates to the operational software for one or more infusion pumps 204. Drug library update database 416 may store one or more drug libraries and/or updates to the one or more drug libraries that are used by the infusion pumps 204 to regulate aspects of drug delivery.

The databases 414, 416 may also store data generated and/or received by the modules 402-412 of the cloud environment 106. Although not illustrated in FIG. 4, the cloud environment 106 may provide other resources such as processors, memory, disk space, network, etc. The modules 402-412 may be hardware components configured to perform one or more of the techniques described herein. Alternatively, the modules 402-412 may be implemented using software instructions stored in physical storage and executed by one or more processors. Although illustrated as separate components, the modules 402-412 may be implemented as one or more hardware components (e.g., a single component, individual components, or any number of components), one or more software components (e.g., a single component, individual components, or any number of components), or any combination thereof.

The cloud environment 106 can be implemented using a commercial cloud services provider (e.g., Amazon Web Services®, Microsoft Azure®, Google Cloud®, and the like). The cloud environment 106 can be implemented using network infrastructure managed by the provider and/or developer of the modules 402-412 shown in FIG. 4. The features and services provided by one of more of the modules 402-412 may be implemented on one or more hardware computing devices as web services consumable via one or more communication networks. One of more of the modules 402-412 can be provided by one or more virtual machines implemented in a hosted computing environment. The hosted computing environment may include one or more rapidly provisioned and released computing resources, such as computing devices, networking devices, and/or storage devices.

Overview of Messaging in the Cloud Environment

Figure 5:
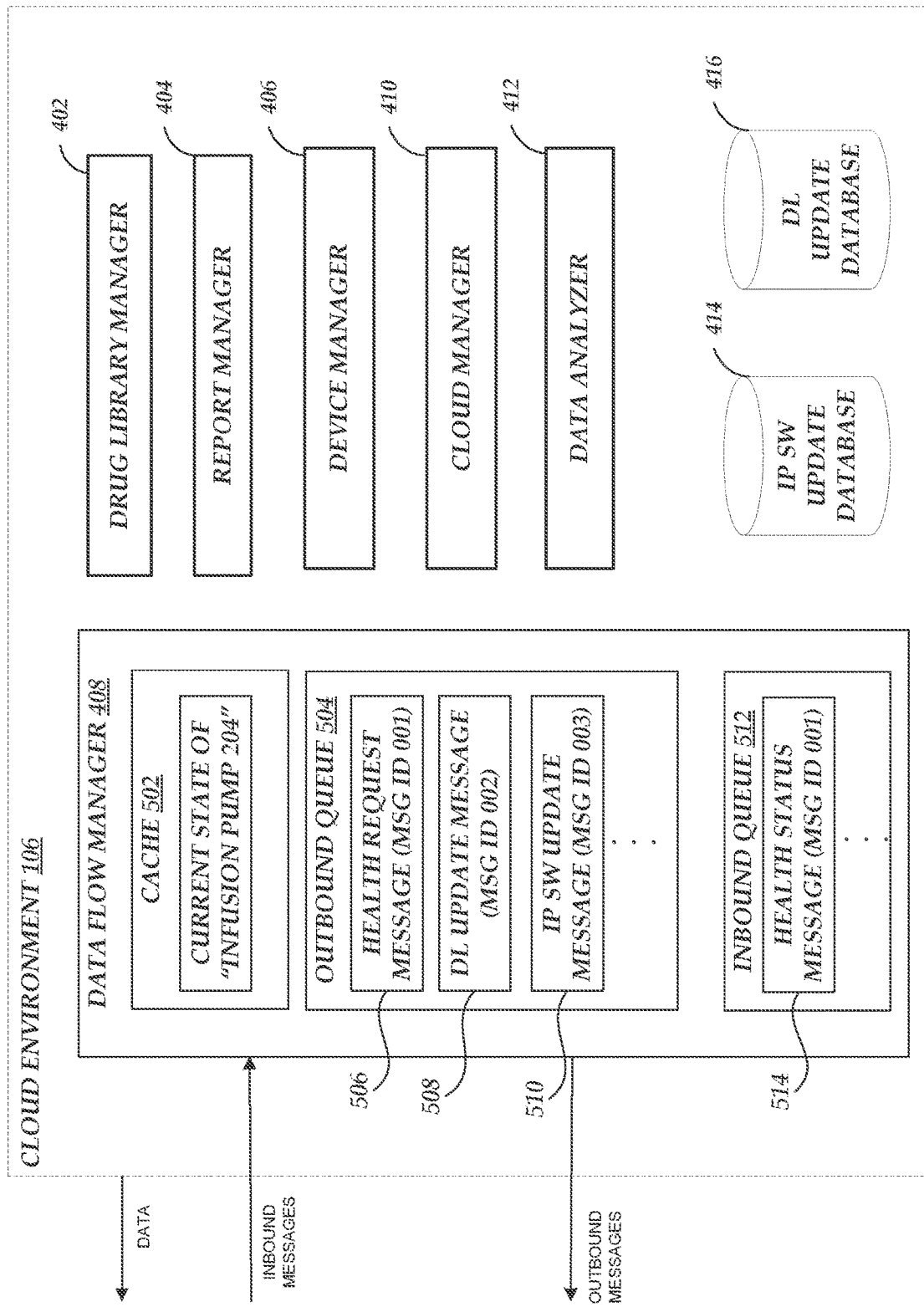
FIG. 5 is a schematic diagram illustrating example components of a data flow manager of a cloud environment.

FIG. 5 illustrates an example of how messages may be received, stored, and transmitted by the cloud environment 106. As shown in FIG. 5, the DFM 408 may include cache 502, outbound queue 504 and inbound queue 512. The outbound queue 504 may include messages to be transmitted to the clinical environment 102. For example, the outbound queue 504 can include a health request message 506, a drug library update message 508 providing a notification that a drug library update is available, and an infusion pump operational software update message 510 providing notification that an update to the infusion pump software is available. When these messages 506, 508, 510 are sent to the connectivity adapter 206, they are stored in the inbound queue 332 of the connectivity adapter 206 as messages 310, 312, respectively, shown in FIG. 3. In other examples, the outbound queue 504 may include command messages (e.g., instructions to update the security settings on the connectivity adapter 206), request messages (e.g., requests for missing messages for logging purposes), log requests, security updates, and the like.

The inbound queue 512 may include messages received from the clinical environment 102. In the example of FIG. 5, the inbound queue 512 includes a health status message 514 providing the status of the connectivity adapter 206. FIG. 3 illustrates the health status message 328 stored in the outbound queue 334 of the connectivity adapter 206 prior to it being sent to the cloud environment 206 and being stored in the inbound queue 512 of the data flow manager 408 as message 514. The inbound and outbound messages may be sent over a message channel of the network 104. The update data from the infusion pump software update database 414 and from the drug library update database 416 may be sent over a data channel of the network 104 that can be separate from the message channel of the network 104.

The cache 502 may store the current state of the infusion pump 204. In some cases, the current state stored in the cache 502 can be identical to the current state stored in the cache 302. In other cases, the current state stored in the cache 502 includes additional information not stored in the cache 302, or vice versa.

The process of reducing the transfer of drug library and operational software files from the cloud environment 106 to infusion pumps 204 is described in greater detail below with reference to FIGS. 6-8D. The process of requesting the health and receiving the health status of the connectivity adapter 206 is described in greater detail below with reference to FIGS. 9A and 9B.

Infusion Pump Drug Library and Software Updates

Hospitals can have thousands of infusion pumps for infusing drugs to patients. Each infusion pump follows rules contained in drug libraries when delivering the drugs to patients. The rules provide boundaries and guidelines for infusion, such as for example, hard dosing limits, soft dosing limits, rates of infusion, etc., for a plurality of infusible drugs. Drug libraries are often updated with new drugs, drugs being infused in new areas of the facility (e.g., neonatal, ICU, NICU), new infusion treatments, and the like. It is desirable that the infusion pumps include drug library updates in order to maintain the highest level of care for patients.

Further, infusion pumps include operational software that controls pump operations. With a hospital or health care system, there may be many different types of infusion pumps, and each type of infusion pump may have different operational software. As with drug libraries, operational software is often updated. The updates may change software functionality or add additional features. It is also desirable that the infusion pumps run the latest software versions in order to maintain the highest level of care for patients.

In a historical infusion pump network and system, each infusion pump may need to access a hospital server and storage where the updates are stored and download drug library and operational software updates. This is time consuming and the volume of network traffic created by potentially thousands of infusion pumps receiving updates can significantly slow down the hospital network, or significantly impact clinical workflows.

However, in an example pump network and system described herein, a connectivity adapter can download the drug library and operational software updates once from cloud based storage and can distribute the updates to infusion pumps when the infusion pumps are available to receive the updates. This relieves network traffic to the server and to the storage storing the updates and reduces the computing time needed to update the infusion pumps over the historical infusion pump networks and systems.

The connectivity adapter can communicate with a plurality of infusion pumps. To reduce local network congestion between the plurality of infusion pumps and the connectivity adapter, the connectivity adapter can stagger blocks of the updates to the infusion pumps.

The connectivity adapter and the cloud environment can communicate over a first network. The first network is the network connection established between the connectivity adapter and the cloud. the first network has two channels: a first channel to receive the update command and a second channel to obtain the update data. The connectivity adapter and each of the plurality of infusion pumps communicate over a second network. The second network is a network connection established between an infusion pump and the connectivity adapter. The second network has two channels: a first channel to receive the update command and a second channel to obtain the update data (e.g., files). This pattern applies to each infusion pump attached to the connected adapter; therefore, there are multiple second network connections for the connectivity adapter.

The update data can be operational software only; drug library data only; or both operational software and drug library information. The user can initiate the update from the cloud environment. A message can be sent from the server in the cloud environment with the update URL that the connectivity adapter can then update to the local URL for use by the infusion pumps as described in greater detail below. Alternatively, the infusion pump can request if there is an update available. The message is routed to the server in the cloud environment. If an update exists, a message can be sent from the cloud environment with the update URL that the connectivity adapter can update to the local URL, in the same manner as when the update is initiated from the cloud environment.

So as to not flood the hospital network, the connectivity adapter can stagger the updates between the connectivity adapter and its connected devices, which can be infusion pumps, medication compounding devices, and the like. For example, connectivity adapter 1 and connectivity adapter 2 can each have 500 connected devices that need to have the update. Each connectivity adapter can schedule the update for a subset of the connected devices, such as for example, 100 devices at a time. The connectivity adapters can be within separate hospital networks.

In another example, connectivity adapter 1 and connectivity adapter 2 can each have 500 connected devices that need to have the update. Connectivity adapter 1 can notify the cloud environment that it can process up to 100 updates and connectivity adapter 2 is too busy to process any updates. The cloud server then schedules updates for 100 of the devices that are connected to connectivity adapter 1. Additionally, connectivity adapter 1 could opt to stagger the update with a subset of the 100 devices as described above.

In another example, connectivity adapter 1 and connectivity adapter 2 can each have 500 connected devices that need to have the update. Both connectivity adapters can exist on the same hospital network. So as to not flood the hospital network, the cloud server will limit the number of updates each connectivity adapter can service concurrently. For example, the cloud server can limit the number of concurrent updates to 100 connected devices, it can then schedule 60 updates for connectivity adapter 1 and 40 updates for connectivity adapter 2. As the updates complete, additional devices can be added such that there are no more than 100 connected devices being updates at a time on the hospital network.

The user, via a user interface, can specific a predetermined number of infusion pumps or connected devices to update. The system can specify a predetermined number of pumps based on network traffic. The system may portion this group into smaller portions. For example, the user may schedules an update for 1000 connected devices. The system can redistribute the predetermined number of connected devices to update in chunks of 100 connected devices. Example methods of staggering updates to the connected devices can be independently responding to requesting devices, staggering groups of connected devices to receive the updates, and staggering the blocks of update data.

The connectivity adapter can determine specific connected devices to receive a different subset of cached blocks during the download of the update data. In another example, each connected device to receive an update can be provided with a local URL which is the location of where to obtain the update data. The connected device then connects to the connectivity adapter independently of any other connected devices and streams the update data. Since each connected device can stream the update data independently, a first connected device in communication with the connectivity adapter could be block 100 while a second connected device could be streaming block 50 of the update. In another example the connectivity adapter can delay the start of the streaming to subsets of the requesting connected devices to reduce the network load. The connectivity adapter can request to deliver an update to the connected devices and each connected device can confirm to the connectivity adapter that it is ready or is not ready to receive an update.

Figure 6:
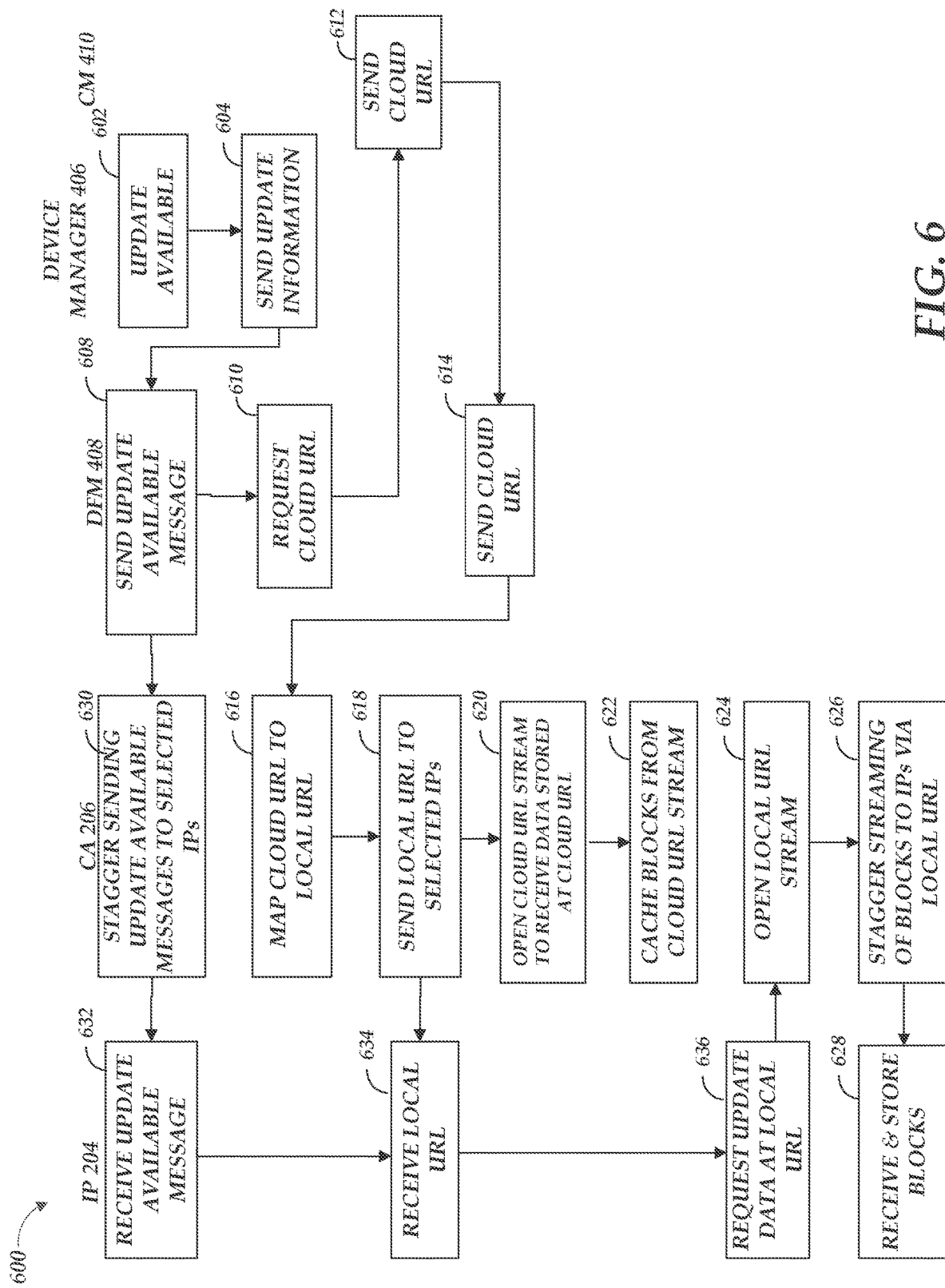
FIG. 6 is a block diagram illustrating an example system for reducing the transfer of drug library and operational software files to a plurality of infusion pumps.

With reference to FIG. 6, an example system 600 for reducing the transfer of drug library and operational software update files to a plurality of infusion pumps (IPs) 204 is described in greater detail. The illustrated system 600 comprises the cloud manager (CM) 410, the device manager 406, the data flow manager (DFM) 408, one or more connectivity adapters (CA) 206, and one or more infusion pumps (IP) 204. The device manager 406 can interface with the user via the cloud user interface 208 (see FIG. 2). For example, the user loads the update data into the CM 410, logs into the device manager 406, and schedules an update for the infusion pumps 204 associated with the system. Scheduling the update includes providing the device manager 406 with update information. The device manager 406 detects the upload of the update data onto the CM 410 and stores the update record (e.g., a cloud URL). The update can be available immediately or can be scheduled for a future time. The update can be a drug library update 416 or the update can be an update of infusion pump operational software 414. The update is not bound by the connectivity adapter 206. Update information can specify one or more filters, such as, for example, specific infusion pumps 204 (i.e., update infusion pumps 1, 2, and 3), specific infusion pump versions (i.e. update all infusion pump operational software version 1.0 to version 1.1), the type(s) of infusion pumps 204 (i.e., update all type 0 infusion pumps 204), and/or the facilities associated with the infusion pumps 204 for which the update 414, 416 applies (i.e., update all infusion pumps 204 in facility XYZ, where XYZ is the facility identifier).

The process of reducing the transfer of drug library and operational software update files to a plurality of infusion pumps (IPs) 204 performed by the system 600 illustrates example algorithm(s) that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process of reducing the transfer of drug library and operational software update files to a plurality of infusion pumps (IPs) 204 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process of reducing the transfer of drug library and operational software update files to a plurality of infusion pumps (IPs) 204 or portions thereof may be implemented on multiple processors, serially or in parallel.

At block 602, the device manager 406 can receive a message from the cloud user interface 208 that the user has scheduled an update. FIG. 6A illustrates an example user interface 650 for scheduling a software update. As shown, the user interface 650 includes fields for selecting a device type, selecting a software version, selecting a facility, and scheduling a start time. User interface 650 can provide an update summary and a device list.

At block 604, the device manager 406 can send the scheduled update information to the DFM 408. The DFM 408 can generate a unique key to identify the scheduled event, as scheduled by the user, for one or more pumps. The update information can include information pertaining to the type of update (e.g., drug library update 416 or operational software update 414), the scheduled availability of the update, the infusion pumps 204 to receive the update, the type of infusion pump 204 to receive the update, facility identifiers, and other associated identifiers. The DFM 408 can wait until the scheduled time to notify the connectivity adapter 206 that the update is available. The DFM 408 can notify the connectivity adapter 206 of the scheduled update and the connectivity adapter 206 can wait until the scheduled time to notify the infusion pumps 204 that the update is available.

The DFM 408 can receive the update information from the device manager 406. At block 608, the DFM 408 can send a message to one or more connectivity adapters 206 indicating that an update is available. The message can be one of the drug library (DL) update message 508 or the infusion pump (IP) software (SW) update message 510. The message can be send over the cloud message channel.

At block 610, the DFM 408 can request a cloud URL from the CM 410. The cloud URL can be the location within the cloud environment 106 storing the update 414, 416. The cloud URL can be a temporary URL having a defined lifetime. At block 612, the CM 410 can send the cloud URL to the DFM 408. At block 614, the DFM 408 can send the cloud URL to the connectivity adapter 206. The cloud URL can be sent over the cloud data channel.

The connectivity adapter 206 can receive the message indicating that an update is available and the cloud URL from the DFM 408. The received message can be one of the DL update message 310 or the IP SW update message 312.

At block 630, the connectivity adapter 206 can send a message to the selected infusion pumps 204 that an update is available. The connectivity adapter 206 can stagger the update notifications to the selected infusion pumps 204. For example, if 100 infusion pumps 204 are scheduled to receive an update, the connectivity adapter 206 may only notify 50 infusion pumps 204 and as individual update downloads complete new updates are scheduled for the remaining infusion pumps 204. The message can be one of the DL update message 314 or the IP SW update message 316. The message can be sent over the local message channel. The selected infusion pumps 204 can be the infusion pumps intended to receive the drug library or operational software update.

At block 616, the connectivity adapter 206 can create a local URL and maps the cloud URL to the local URL. The local URL can be a URL identifying a location in the connectivity adapter 206 within the clinical environment 102. At block 618, the connectivity adapter 206 can send the local URL to the infusion pumps 204 identified in the update available message. The local URL can be sent over the local data channel.

At block 620, the connectivity adapter 206 can open a cloud URL stream to receive the update data stored at the cloud URL. The update data can be streamed from storage 414, 416 at the cloud URL over the cloud data channel. The messaging between the connectivity adapter 206 and the DFM 408 can occur on the cloud message channel that is separate from the cloud data channel. Thus, the cloud data channel can solve the problem of data packet prioritization because the data streaming, which is occurring on a separate channel, does not interfere with the infusion pump clinical messaging. Further, the cloud data channel can strengthen and simplify the security of the network by allowing the infusion pumps 204 to receive data over a secured isolated virtual local network (VLAN) that is not exposed to public networks. Advantageously, the infusion pumps 204 can request and receive the update data from the connectivity adapter 206 should the network connection between the connectivity adapter 206 and cloud environment 106 become unavailable because the updates are stored at the connectivity adapter 206.

The connectivity adapter 206 can be pre-notified of an available update, stream the update data before the scheduled update time, and notify the infusion pumps 204 of the available update at the scheduled time. This can also provide the advantage of being able to update the infusion pumps 204 at the scheduled update time should the network connection with the cloud environment 106 become unavailable at the scheduled update time.

At block 622, the connectivity adapter 206 can cache blocks of the streaming update data in the cache 302. The connectivity adapter 206 can associate data in the cache 302 with the local URL. Once the update is stored in the cache 302 at the connectivity adapter 206, the cloud data channel between the connectivity adapter 206 and the DFM 408 may no longer be needed. This can reduce network activity as the cloud environment 106 does not need to be accessed to individually update each infusion pump 204.

At block 632, the selected infusion pumps 204 can receive the message 314, 316 from the connectivity adapter 206 that an update is available. At block 634, the infusion pumps 204 can receive the local URL from the connectivity adapter 206.

At block 636, the selected infusion pumps 204 can request the update data at the local URL from the connectivity adapter 206. The request can include an HTTP multi-part GET request. Each infusion pump 204 can request the update data when it is available to receive the update data.

The update data from the connectivity adapter 206 to the infusion pump 204 can be streamed over the local data channel within the local network. The messaging between the connectivity adapter 206 and the infusion pumps 204 can occur over the local message channel that is separate from the local data channel. Thus, the local data channel within the local or hospital network can also solve the problem of data packet prioritization because the data streaming, which is occurring on a separate channel does not interfere with the clinical infusion pump messaging on the local message channel. Another advantage of separating the messages and the data onto a local message channel and a local data channel, respectively, can be allowing the infusion pump CE 324 to actively download into its storage 322 large files, which can be, for example, 300 MBs or more, without interrupting the infusion pump MCU 326 which is performing clinical functions. Once the clinical functions are complete, the user can initiate the update without waiting for the update data to be downloaded.

At block 624, the connectivity adapter 206 can open the local URL stream. At block 626, the connectivity adapter 206 can stagger streaming of the blocks of update data via the local URL. The connectivity adapter 206 can stagger the update data in blocks by independently responding to requests from the group of infusion pumps 204. For example, infusion pump 204A can be downloading block five and infusion pump 204B can be downloading block seven from the local URL cache 302, while the connectivity adapter 206 can be downloading block ten from the cloud URL.

As described above at block 630, the connectivity adapter 206 can stagger update notifications to the infusion pumps 204. For example, if 100 infusion pumps 204 are scheduled to receive an update, the connectivity adapter 206 may only notify 50 infusion pumps 204 and as individual update downloads complete new updates are scheduled for the remaining infusion pumps 204.

The infusion pumps 204 can also include functionality to avoid network slowdowns. The infusion pumps 204 can check within its memory 322 to determine whether the available update is already there. If the update is available, the infusion pump 204 may not request the update. The infusion pump 204 can check within its communication engine 204, for example, to determine whether another update is already pending. If another update is pending, the infusion pump 204 may not request the update. The system 600 may not permit a drug library update and an operational software update to occur at the same or near to the same time.

The infusion pump 204 can utilize an exponential backoff procedure when requesting the update data from the connectivity adapter 206. For example, when the request from the infusion pump 204 for the update data is unfilled or ignored, the infusion pump 204 can re-request the update data according to a process, such as an exponential backoff process to prevent network congestion. In an exponential backoff process, the rate at which the infusion pump 204 sends the re-requests can be decreased gradually in order to find an acceptable request rate. The infusion pump 204 can re-request the update data randomly to prevent network congestion.

At block 628, the infusion pump 204 can receive and store the blocks of update data in the memory 322. As discussed above, the update data can be an updated or new drug library, updated operational software for the infusion pump 204, which may include one or more of application software, language packs, security updates, and device configuration, digital certificates, and/or the like.

The infusion pump 204 can initiate the request to the connectivity adapter 206 for update data, such as an updated drug library, without being notified of an available update. For example, the infusion pump 204 can send a request to the connectivity adapter 206 for a known missing drug library, or to ask if an update is available. The connectivity adapter 206 can store a plurality of drug libraries, including historical versions of drug libraries.

Figure 7:
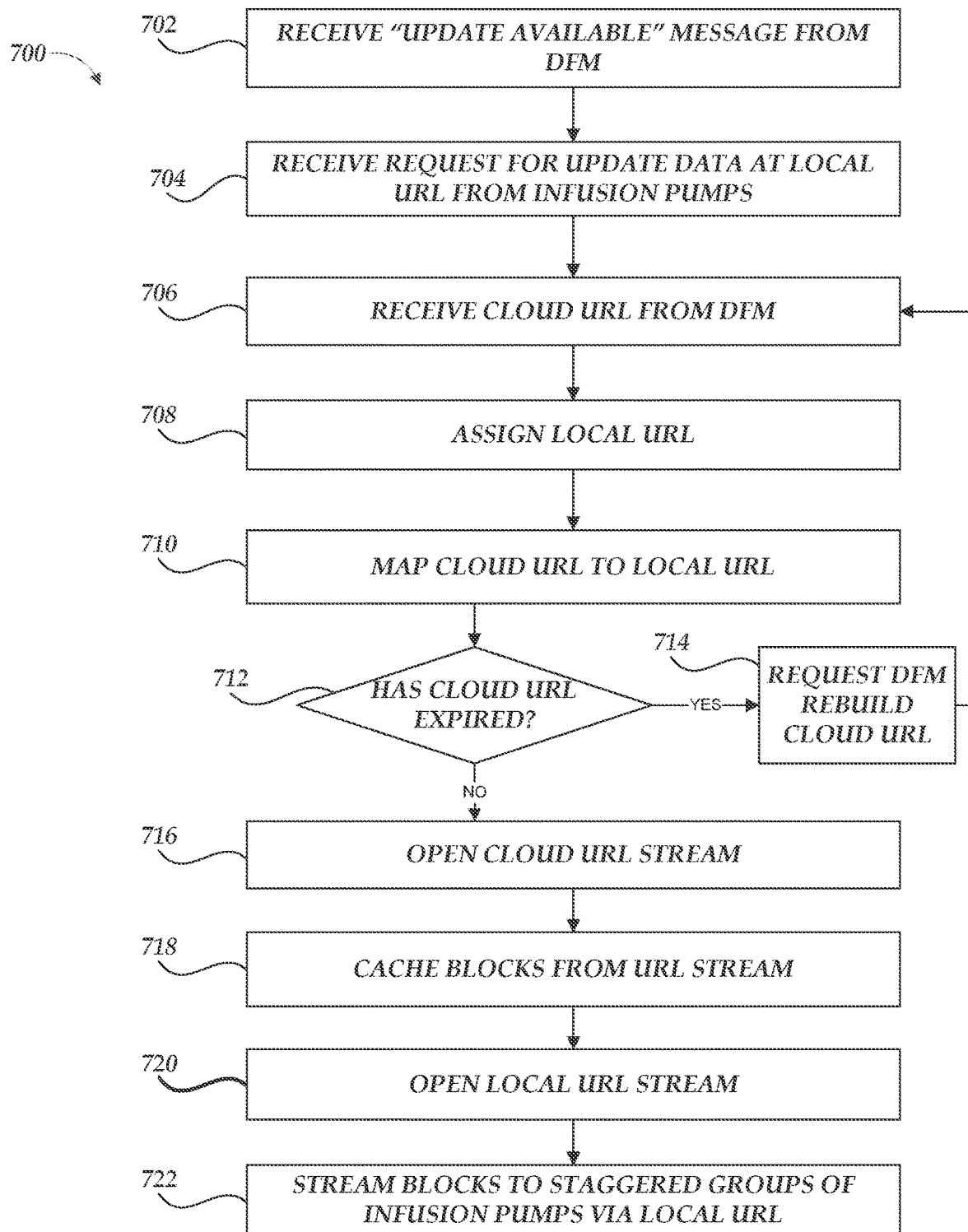
FIG. 7 is a flow chart of an example process to reduce the transfer of drug library and operational software files to a plurality of infusion pumps.

With reference to FIG. 7, an example process 700 to reduce the transfer of drug library and operational software files to a plurality of infusion pumps 204 is described in greater detail. The process 700 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process 700 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process 700 or portions thereof may be implemented on multiple processors, serially or in parallel. For convenience, the steps of the example process 700 are described as being performed by the connectivity adapter 206.

At block 702, the connectivity adapter 206 can receive the drug library update message 310 or the infusion pump operational software update message 312.

The connectivity adapter 206 can notify the infusion pumps 204 that an update is available at the local URL. The connectivity adapter 206 can send a drug library update message 314 or a software update message 316 over the local message channel associated with the local network. The connectivity adapter 206 can stagger notifying the infusion pumps 204 by notifying a portion of the selected infusion pumps 204 and notifying subsequent portion of the selected infusion pumps 204 as individual update downloads complete.

At block 704, the connectivity adapter 206 can receive request(s) from the infusion pump(s) 204 for the update data at the local URL.

At block 706, the connectivity adapter 206 can receive the cloud URL from the DFM 408. The cloud URL can have an expiration time.

At block 708, the connectivity adapter 206 can assign a local URL. The connectivity adapter 206 can create the local URL. At block 710, the connectivity adapter 206 can map the cloud URL to the local URL.

At block 712, the connectivity adapter 206 can determine whether the cloud URL has expired. If the cloud URL is active, the process 700 can move to block 716.

If the cloud URL has expired, the process can move to block 714. At block 714, the connectivity adapter 206 can request that the DFM 408 rebuild the cloud URL. The DFM can determine a new cloud URL and can send the new cloud URL to the connectivity adapter 206. The process 700 can move to block 704 and repeat blocks 704-712 for the new cloud URL.

At block 716, the connectivity adapter 206 can open the cloud URL stream and at block 718, can cache the blocks of update data from the URL stream over the cloud data channel associated with the network 104.

At block 720, in response to receiving requests for the update data from the infusion pumps 204, the connectivity adapter 206 can open the local URL stream. At block 722, the connectivity adapter 206 can stream blocks of update data to staggered groups of infusion pumps 204. The blocks of update data can be streamed over the local data channel to the infusion pumps 204. Staggering can be performed in a variety of ways. For example, the connectivity adapter 206 can stream blocks of data in parallel to a small group of infusion pumps 204. If the infusion pump's initial request for data is rejected or ignored, the infusion pumps 204 can re-request the update data at a rate as determined by an exponential backoff process.

As described above, the updates can include operational software updates or drug library updates. The receiving and storing of the blocks of update data can occur in the background when the infusion pump 204 is operating. However, the installation and running of the updates can occur under controlled conditions, such as when the infusion pump 204 is not being used to infuse medication to patients.

Figure 8:
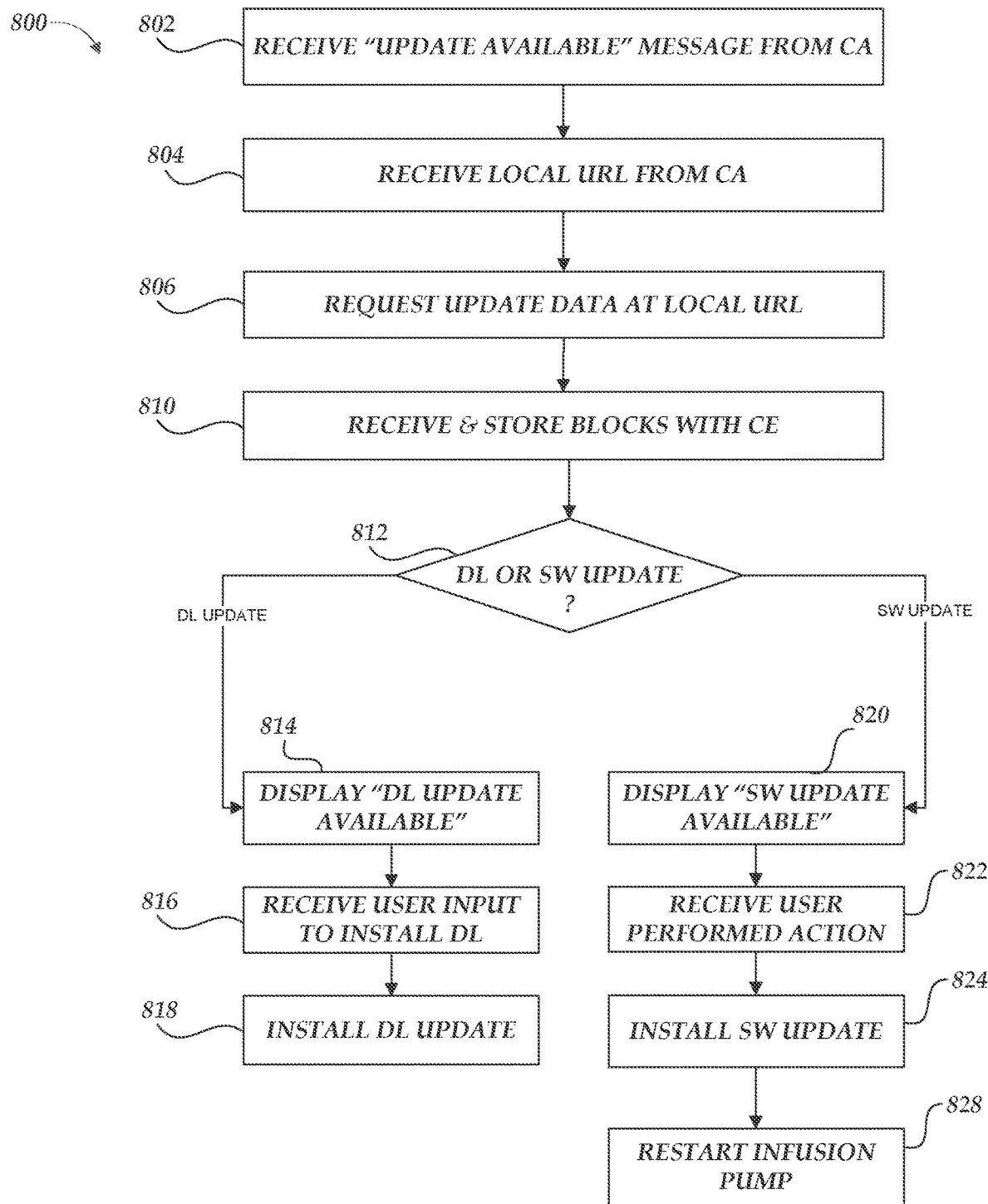
FIG. 8 is a flow chart of an example process to install drug library and operational software updates by an infusion pump.

With reference to FIG. 8, an example process 800 of infusion pump 204 installation of drug library and operational software updates is described in greater detail. The process 800 illustrates an example algorithm that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process 800 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102. The executable instructions may then be executed by a hardware-based computer processor (e.g., a central processing unit or "CPU") of the computing device. The process 800 or portions thereof may be implemented on multiple processors, serially or in parallel. For convenience, the steps of the example process 800 are described as being performed by the infusion pump 204.

At block 802, the infusion pump 204 can receive an update message 314, 316 from the connectivity adapter 206. At block 804, the infusion pump 204 can receive the local URL from the connectivity adapter 206. At block 806, the infusion pump 204 can request the update data at the local URL from the connectivity adapter 206. At block 810, the infusion pump 204 can receive blocks of the update data over the local data channel and can store in the memory 322 the blocks of update data received from the connectivity adapter 206.

At block 812, the infusion pump 204 can determine whether the update comprises a drug library update or an operational software update. The update available message received from the connectivity adapter 206 can include information as to the type of update, such as an operational software update or a data library update.

When the update is a drug library update, the process 800 can move to block 814. At block 814, the infusion pump 204 can display on its display a message to the user that a drug library update is available. Upon power down, the infusion pump 204 can displays the message that a drug library is available and can provide a user prompt (yes/no) to accept or decline the drug library update. The user may decline updating the drug library for a predetermined number of attempts. The drug library update can occur automatically upon power down of the infusion pump 204.

Figure 8A:
FIG. 8A illustrates an example user interface for installing a new drug library.

FIG. 8A illustrates an example infusion pump user interface 850 for installing a new drug library. As shown, infusion pump user interface 850 can notify the user that a new drug library is available, provide an estimate of the installation time, and provide fields for installing the new drug library now or at shutdown of the infusion pump 204.

At block 816, the infusion pump 204 can receive the user input to install the drug library and at block 818, the infusion pump can install the drug library. The drug library may be available after a reboot of the infusion pump 204.

When the update is an operational software update, the process 800 can move to block 820. At block 820, the infusion pump 204 can display on its display a message to the user that an operational software update is available. Upon power down, the infusion pump 204 can display the message that operational software update is available and can provide a user prompt to request the update. The user may decline updating the operational software for a predetermined number of attempts. The operational software update can occur automatically upon power down of the infusion pump 204. The user can initiate the operational software update when the infusion pump 204 is operating in a clinical mode. The infusion pump 204 can enter a non-clinical operational mode before the user can initiate an operational software update. The infusion pump 204 can enter a non-clinical operational mode before the user can initiate an operational software update. The non-clinical operational mode can be referred to as the Biomed mode.

Figure 8B:
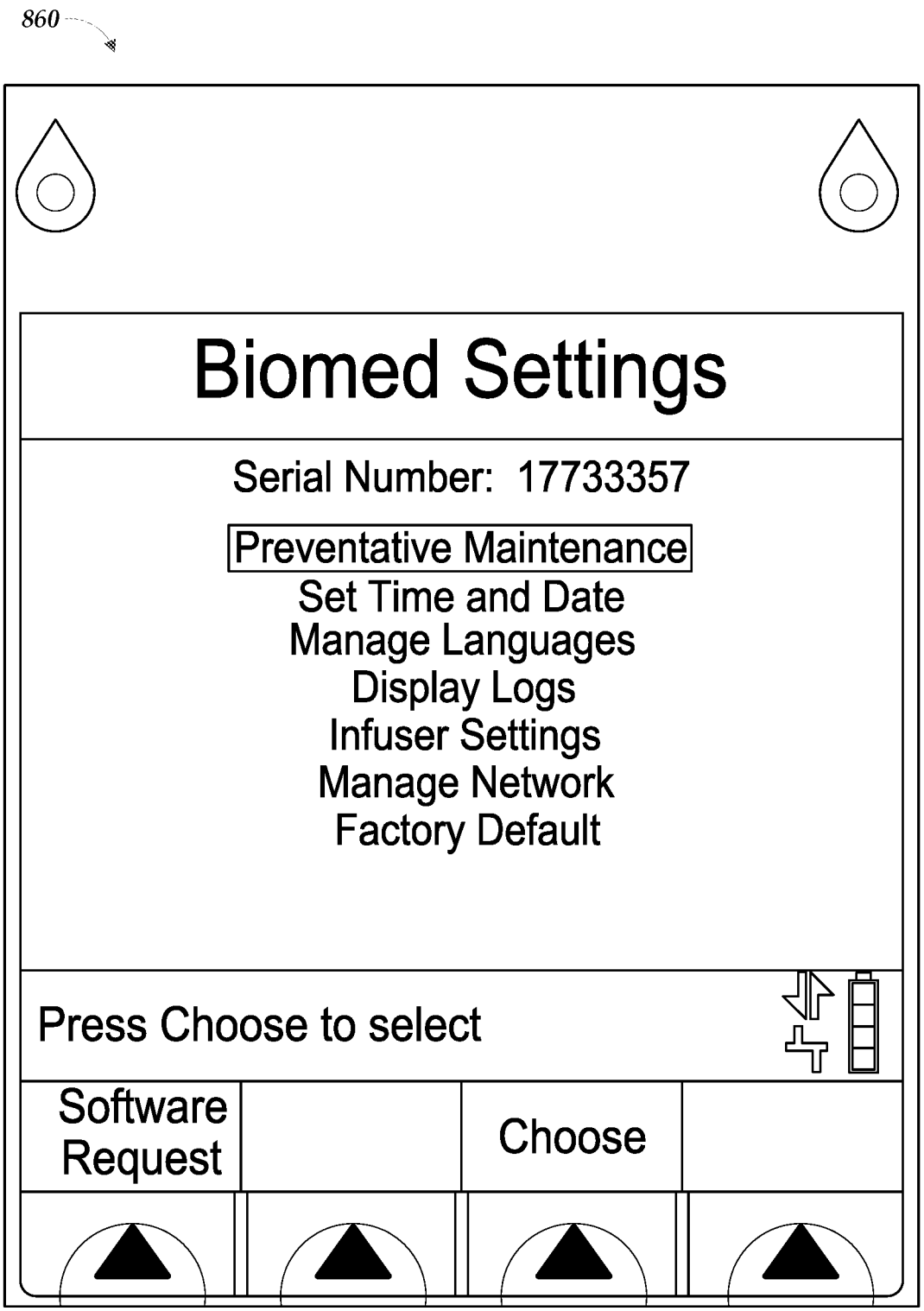
FIG. 8B illustrates an example user interface for installing an operational software update.

FIG. 8B illustrates an example user interface 860 for installing an operational software update. As shown infusion pump user interface 860 can display the serial number of the infusion pump 204 and can prompt the user to "select preventative maintenance", "set time and date", "manage languages", "display logs", "infuser settings", "manage network", "factory default", and "software request".

Figure 8C:
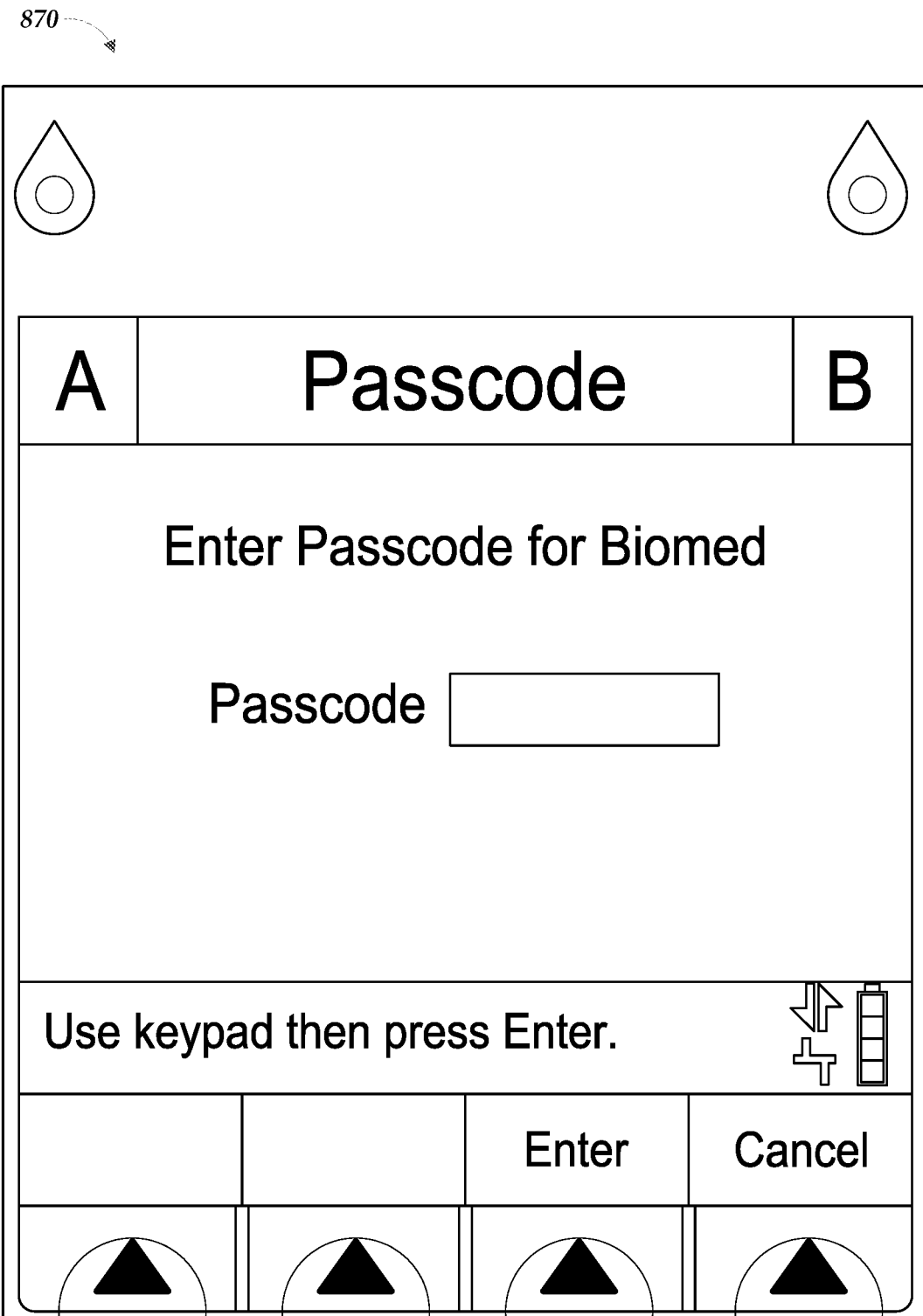
FIG. 8C illustrates an example user interface for entering proper credentials prior to initiating an operational software update.

It may be desirable that the infusion pump 204 not be in clinical use when the operational software is updated. At block 822, the infusion pump 204 can receive the user performed action(s). For example, the user can enter "Biomed" mode using proper credentials before performing the software update operation. FIG. 8C illustrates an example infusion pump user interface 870 for entering proper credentials prior to initiating an operational software update.

Figure 8D:
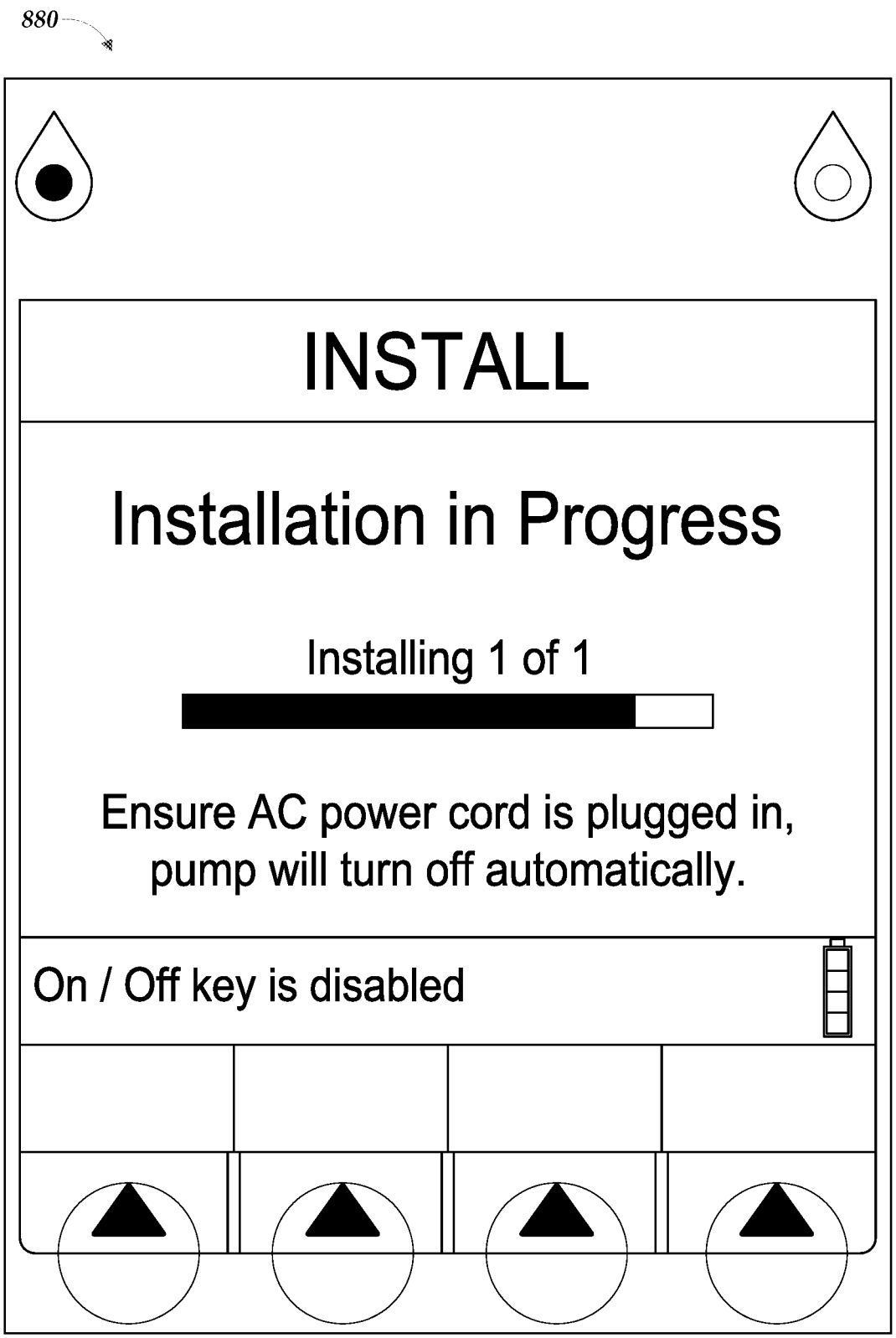
FIG. 8D illustrates an example user interface for notifying the user of the progress of the operational software installation.

At block 824, the infusion pump 204 can install the operational software update and at block 828, the infusion pump 204 can reboot. FIG. 8D illustrates an example infusion pump user interface 870 for notifying the user of the progress of the operational software installation. The infusion pump 204 via the display may notify the user that the operational software has been updated.

Health Status of Connectivity Adapters

Connectivity adapters that are responding too slowly can affect the overall performance of the system 100. Further, the communication between the connectivity adapter 206 and the infusion pumps 204 can be important to provide the infusion pumps 204 with revised operating software and updated drug libraries. Improperly operating connectivity adapters 206 can over fill queues and utilize additional computing time. It can be important to monitor the health of the connectivity adapters 206 and correct any problems to reduce computing time and memory usage.

Figure 9A:
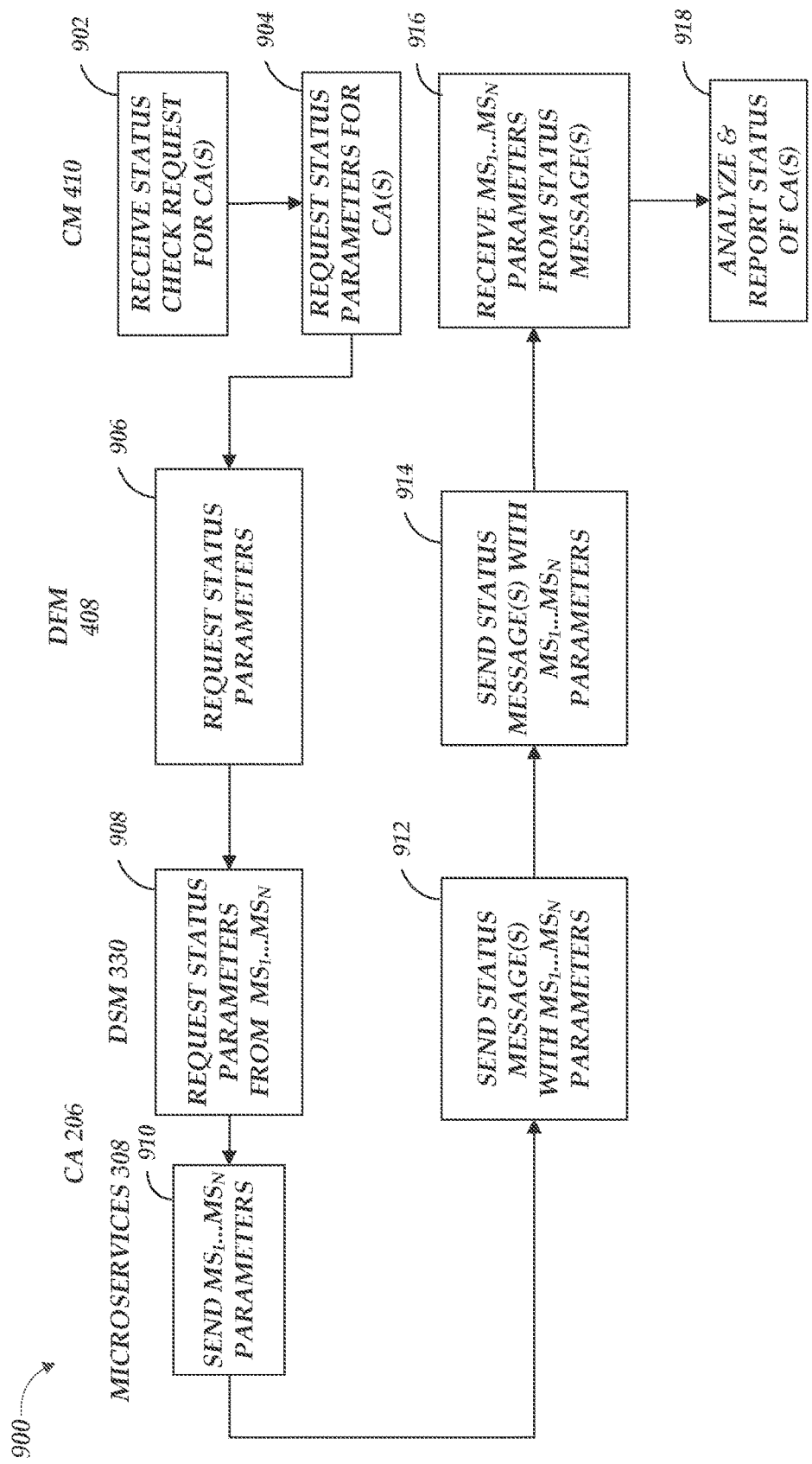
FIG. 9A is a block diagram illustrating an example request-driven system to check the status of connectivity adapters.

With reference to FIG. 9A, an example request-driven system 900 to check the status or health of connectivity adapters 206 is described in greater detail. The illustrated system 900 can comprise the cloud manager (CM) 410, the data flow manager (DFM) 408 and one or more connectivity adapters (CA) 206. The CM 410 can interface with the user via the cloud user interface 208, for example. Each connectivity adapter 206 can include one or more microservices 308 and a device status manager (DSM) 324. Each microservice 308 can monitor a parameter associated with the operation of the connectivity adapter 206. The microservices 308 can create containers of unstructured data associated with the monitored parameters.

Each microservice 308 can perform a function or service associated with the operation of the connectivity adapter 206 and can monitor the performance of that function or service. For example, a microservice 308 can operate and monitor the outbound message queue 334 of the connectivity adapter 206. The microservice 308 associated with the outbound message queue 334 can receive the outbound message, write the message to the outbound message queue 334, set up the communication with the DFM 408 or the infusion pump 204, and send the message. The microservice 308 associated with the outbound message queue 334 may also monitor the latency, determine, based on a received acknowledgement, how long the outgoing message took to be received, keep track of the size of the outbound message queue 334, and the like.

Other examples of microservices 308 associated with the operation of the connectivity adapter 206 can be, but not limited to, resource manager to manage the connectivity adapter resources, device status service to manage the connectivity adapter status, drug library service to manage the drug libraries stored at the connectivity adapter 206, and configuration manager to manage the configuration of the connectivity adapter. The microservices 308 can also monitor parameters associated with their functionality, such as, but not limited to the average message rate, the spike message rate, the response rate for messages from the DFM 408, the response rate for messages from the infusion pumps 204, the length of message queues 332, 334, latency, CPU load, disk space, available memory, the amount of memory used, bandwidth, error levels, and the like.

The request-driven system 900 illustrated in FIG. 9A can be considered a demand driven system. The user can request via the cloud user interface 208 a current status of at least a portion of the connectivity adapters 206 within the clinical environment 102.

The process of checking the status or health of connectivity adapters 206 performed by the system 900 illustrates example algorithm(s) that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process of checking the status or health of connectivity adapters 206 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process of checking the status or health of connectivity adapters 206 or portions thereof may be implemented on multiple processors, serially or in parallel.

At block 902, the CM 410 can receive an indication of the user's request for the current status of the connectivity adapters 206. At block 904, the CM 410 can send the request for the current status of the connectivity adapters to the DFM 408. At block 906, the DFM 408 can receive the request from the CM 410 and can send a request for the monitored parameters, such as the health request message 506 to the connectivity adapters 206. The DFM 408 can send the health request message 506 to each of the connectivity adapters 204 within the clinical environment 102. The DFM 408 can send the health request message 506 to a subset of connectivity adapters 206 that are specified in the user request.

At block 908, the DSM 330 of the connectivity adapter 206 can receive the request for the parameters, such as the health request message 326, and can internally request the monitored parameters from the microservices 308 operating within the connectivity adapter 206. At block 910, each of the microservices 308 can receive the parameter request and can send the parameter information to the DSM 330.

At block 912, the DSM 330 can receive the parameter information from the microservices 308 and can send one or more status messages with the parameter information, such as the health status message 328 to the DFM 408. The DSM 330 can receive the parameter information from the microservices 308 and can combine the parameter information into a single status message 328. The DSM 330 can use the general data set message format and can format the parameter information into a general data set message. The DSM 330 can send multiple status messages 328 to the DFM 408, where each of the multiple status messages 328 can include information from one or more parameters.

At block 914, the DFM 408 can receive the one or more status messages from the connectivity adapters 206 and can send the status messages to the CM 410. At block 916, the CM 410 can receive the status messages. At block 910, the cloud environment 106 can analyze and report the status of the connectivity adapters 206 to the user. The user can receive an email, a SMS message, or the like, from the cloud environment 106.

The CM 410 can report the parameters to the user. The CM 410 can analyze the parameters and report the status of the connectivity adapters 206 to the user. For example, if the parameters are within a threshold, the CM 410 can report the status as "healthy", and if one or more parameters are greater than a threshold, the CM 410 can report the status as "not healthy". The threshold can be a numerical value for the monitored parameter or the threshold can be an event threshold indicating a number of events occurring for the monitored parameter.

With reference to FIG. 9B, an example self-reporting system 950 to provide the status of connectivity adapters 206 is described in greater detail. Similar to FIG. 9A, the illustrated system 950 of FIG. 9B can comprise the cloud manager (CM) 410, the data flow manager (DFM) 408 and one or more connectivity adapters (CA) 206 and each connectivity adapter 206 can include the one or more microservices 308 and the device status manager (DSM) 330, as described above.

The self-reporting system illustrated in FIG. 9B can be considered a supply driven system. Instead of the status request being generated by the user at the cloud user interface 208, the connectivity adapters 206 can store configuration thresholds and when a threshold is met, the connectivity adapter 206 can send the parameter information to the CM 410, which can in turn report the status or health of the connectivity adapter 206 to the user. The threshold can be a numerical value for the monitored parameter or the threshold can be an event threshold indicating a number of events occurring for the monitored parameter. The process of reporting the status or health of the connectivity adapter 206 performed by the system 950 illustrates example algorithm(s) that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process of reporting the status or health of the connectivity adapter 206 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process of reporting the status or health of the connectivity adapter 206 or portions thereof may be implemented on multiple processors, serially or in parallel.

At block 952, the microservices 308 can be monitoring their associated parameters and one or more of the monitored parameters can exceed a threshold. At block 954, the microservices 308 associated with the one or more parameters that have exceeded the threshold can send the parameter information for the one or more parameters to the DSM 330. At block 956, the DSM 330 can determine the status of the connectivity adapter 206 based at least in part on the monitored parameters. At block 958, the DSM 330 can send a status message, such as the health status message 328, with the parameter information of the one or more the microservices 308.

For example, the connectivity adapter 206 can include a configuration file with the thresholds for the monitored parameters. The microservices 308 can query the configuration file. When the threshold for a monitored parameter is met, the DSM 330 can be notified to send a status message to the DFM 408.

The DSM 408 can receive the parameter information from the microservices 308 and combine the parameter information into a single status message 328. The DSM 330 can use the general data set message format and formats the parameter information into a general data set message. The DSM can send individual status messages 328 when an event threshold is triggered.

To control sending status messages when the parameter is fluctuating around the threshold, the DSM 330 can monitor the status messages 328 and discard status messages 328 if a recently sent message is being repeated. This can avoid sending a plurality of messages for the same error in a short time, which can slow the network down. For example, if the threshold is 79 and the parameter is fluctuating between 78 and 80, the DSM 330 can wait an amount of time before sending another status message 328 for that parameter. The DSM 330 can wait until a number of status messages for the same parameter occur before sending the message 328 to the DFM 408.

The DSM 330 can reset the microservice 308 that has reported parameters meeting or exceeding a threshold. This can occur before sending the status message 328 to the DFM 408 or after sending the status message 328 to the DFM 408. The connectivity adapter 206 can reset itself when the parameter information indicates that one or more parameter thresholds are met or exceeded.

At block 960, the DFM 408 can receive the status message from the DSM 330 of the connectivity adapter 206 and can send a status message with the status of the connectivity adapter 206 to the CM 410. At block 962, the CM 410 can receive the status message. At block 964, the CM 410 can report the parameter information to the user. The CM 410 can analyze and report the parameter information to the user. The user can receive an email, a SMS message, or the like, from the CM 410.

Once poor performance of the connectivity adapter is detected, the connectivity adapter or the cloud server, or both the connectivity adapter and the cloud server can automatically perform tasks in response to the detected parameters exceeding a threshold. For example, the connectivity adapter can reset itself, the cloud server can cause the connectivity adapter to reset. The cloud server can include an algorithm that when tripped by detected poor performance of the connectivity adapter, can send a signal or message to the connectivity adapter to reboot, which may correct the issue. Another automated task may be to send an email when disk space is running low. Additionally, the CA could reset itself when certain thresholds are triggered. Once the number of connected devices exceeds a threshold, the connectivity adapter can send a notification to the cloud server and the connectivity adapter can begin to reject connections from new devices. In another example, if the queue size exceeds a threshold, the system begins to disconnect connected devices until the queue is restored to a level below the threshold.

Examples

A system can be configured to provide update data to a plurality of infusion pumps within a clinical environment. The system can comprise a plurality of infusion pumps configured to deliver medication to one or more patients, where each respective infusion pump of the plurality of infusion pumps can comprise a memory configured to store operational software and one or more drug libraries; an asset lifecycle manager comprising computer hardware and can be configured to receive user input comprising update information that includes at least a location of update data, the update data being one of an operational software update and a drug library update; a data flow manager comprising computer hardware and configured to receive an update notification and a cloud URL associated with the location of the update data from the asset lifecycle manager; and a connectivity adapter comprising computer hardware and memory configured to store at least the update data.

The connectivity adapter can in communication with the plurality of infusion pumps over a first network within a clinical environment and the connectivity adapter can be further in communication with the data flow manager over a second network outside of the clinical environment. The connectivity adapter can be configured to receive the update notification and the cloud URL from the data flow manager over a first communication channel of the second network;

map the cloud URL to a local URL; open a stream to receive the update data stored at the cloud URL, the update data can be received over a second communication channel of the second network; cache blocks of the update data in the connectivity adapter memory that is associated with the local URL; receive a request from at least one infusion pump of the plurality of infusion pumps over a first communication channel of the first network for the update data at the local URL; and stagger streaming blocks of the update data to the at least one infusion pump over a second communication channel of the first network.

The connectivity adapter can be further configured to send the update notification and the local URL associated with the location of the update data to at least a portion of the plurality of infusion pumps. The update information can further include a schedule indicating when the update data is available. The cloud URL can be accessible for a duration of time.

Staggering streaming blocks of update data can comprise streaming blocks of update data in parallel to staggered groups of the one or more infusion pumps. The one or more infusion pumps can be further configured to re-request the update data until the update data is sent, a frequency of re-requests occurring according to an exponential backoff process. The one or more infusion pumps can be further configured to determine whether the memory associated with the respective infusion pump of the one or more infusion pumps includes the update data prior to requesting the update data. For example, if the infusion pump 204 has the operational software update stored in memory 322, the infusion pump 204 does not need to download the update from the connectivity adapter 204. The CE 324 can update the MCU 326 with the update data stored in the memory 322.

The connectivity adapter can be further configured to send status parameters associated with microservices operating within the connectivity adapter. The connectivity adapter can be further configured to receive a request for status, and in response to the request for status, can send status parameters associated with microservices operating within the connectivity adapter. The connectivity adapter can be further configured to send status parameters associated with microservices operating within the connectivity adapter when at least one status parameter exceeds a threshold.

A method can provide update data to a plurality of infusion pumps within a clinical environment. The method can comprise receiving user input comprising update information that includes at least a location of update data in a cloud environment, where the update data being one of an operational software update and a drug library update, and where the location of the update data in the cloud environment associated with a cloud URL; receiving an update notification responsive to the user input and receiving the cloud URL over a first communication channel of a network associated with the cloud environment; and mapping the cloud URL to a local URL; opening a stream to receive the update data stored at the cloud URL, where the update data received over a second communication channel of the network associated with the cloud environment;

The method can further comprise caching blocks of the update data in memory that is associated with the local URL; receiving a request for the update data at the local URL from at least one infusion pump of a plurality of infusion pumps over a first communication channel of a network associated with a clinical environment. The plurality of infusion pumps can be configured to deliver medication to one or more patients. Each respective infusion pump of the plurality of infusion pumps can comprise a memory configured to store operational software and one or more drug libraries. The method can further comprise staggering streaming blocks of the update data to the at least one infusion pump over a second communication channel of network associated with the clinical environment.

Embodiments of the present disclosure can be defined by the following non-limiting clauses:

Clause 1. A system configured to provide update data to a plurality of infusion pumps configured to deliver medication to one or more patients within a clinical environment, each infusion pump of the plurality of infusion pumps comprising memory configured to store operational software and one or more drug libraries, the system comprising:

a server configured to receive user input comprising at least a first location of update data, the first location being outside of the clinical environment; and an apparatus comprising computer hardware and memory configured to store at least the update data, the apparatus in communication with the server over a first network that provides communication outside of the clinical environment, the memory further storing instructions that, when executed by the computer hardware, configure the apparatus to:

receive the first location of the update data from the server over a first communication channel of the first network;

receive the update data from the first location over a second communication channel of the first network; and store blocks of the update data at a second location that is within the clinical environment, wherein the stored blocks of update data are available for transmission to one or more infusion pumps of the plurality of infusion pumps over a second network that is within the clinical environment.

Clause 2. The system of Clause 1 wherein the stored blocks of data are stored in cache memory.

Clause 3. The system of Clause 1 wherein the update data is at least one of an operational software update and a drug library update.

Clause 4. The system of Clause 1 wherein the first location corresponds to a cloud URL and the second location corresponds to a local URL, the apparatus further configured to map the cloud URL to the local URL.

Clause 5. The system of Clause 4 wherein the cloud URL is a temporary URL having a defined lifetime.

Clause 6. The system of Clause 4 wherein the plurality of infusion pumps do not have network access to the cloud URL, the local URL providing access to the update data.

Clause 7. The system of Clause 1 wherein the first location is a temporary location having a defined lifetime.

Clause 8. The system of Clause 1 wherein the apparatus is further configured to, in response to receiving a request for the update data, open a local URL stream.

Clause 9. The system of Clause 1 wherein the apparatus is further configured to notify at least a portion of the one or more infusion pumps that the update data is available.

Clause 10. The system of Clause 8 wherein the user input further includes filter information, and wherein the apparatus is further configured to determine at least a portion of the one or more infusion pumps based at least in part of the filter information.

Clause 11. The system of Clause 9 wherein the filter information includes at least one of an indication of a specific infusion pump, an indication of a specific version of an infusion pump, or an indication of a specific facility.

Clause 12. The system of Clause 1 wherein the user input further includes a schedule indicating when the update data is available.

Clause 13. A method to provide update data to a plurality of infusion pumps that are configured to deliver medication to one or more patients within a clinical environment, each infusion pump of the plurality of infusion pumps comprising memory configured to store operational software and one or more drug libraries, the method comprising:

receiving user input comprising at least a first location of update data, the first location being outside of the clinical environment;

at an apparatus configured to communicate with the plurality of infusion pumps over a first network that is within the clinical environment:

receiving the first location of the update data over a first communication channel of a second network that provides communication outside of the clinical environment;

receiving the update data from the first location over a second communication channel of the second network; and storing blocks of the update data at a second location that is within the clinical environment, wherein the stored blocks of update data are available for transmission to one or more infusion pumps of the plurality of infusion pumps over the first network within the clinical environment.

Clause 14. The method of Clause 13 wherein the user input further includes a schedule indicating when the update data is available.

Clause 15. The method of Clause 12 wherein the apparatus is further configured to notify at least a portion of the one or more infusion pumps that the update data is available.

Clause 16. The method of Clause 15 wherein the user input further includes filter information, and wherein the apparatus is further configured to determine at least a portion of the one or more infusion pumps based at least in part of the filter information.

Clause 17. The method of Clause 16 wherein the filter information includes at least one of an indication of a specific infusion pump, an indication of a specific version of an infusion pump, or an indication of a specific facility.

Clause 18. A method to provide update data to a plurality of infusion pumps that are configured to deliver medication to one or more patients within a clinical environment, each infusion pump of the plurality of infusion pumps comprising memory configured to store operational software and one or more drug libraries, the method comprising:

at an apparatus configured to communicate with the plurality of infusion pumps over a first network that is within the clinical environment:

requesting update data, the update data having a first location that is outside of the clinical environment;

receiving the first location of the update data over a first communication channel of a second network that provides communication outside of the clinical environment;

receiving the update data from the first location over a second communication channel of the second network; and storing blocks of the update data at a second location that is within the clinical environment, wherein the stored blocks of update data are available for transmission to one or more infusion pumps of the plurality of infusion pumps over the first network within the clinical environment.

Clause 19. The method of Clause 18 wherein the first location corresponds to a cloud URL and the second location corresponds to a local URL, the apparatus further configured to map the cloud URL to the local URL.

Clause 20. The system of Clause 19 wherein the cloud URL is a temporary URL having a defined lifetime.

Clause 21. The system of Clause 10 wherein the plurality of infusion pumps do not have network access to the cloud URL, the local URL providing access to the update data.

Clause 22. The system of Clause 18 wherein the first location is a temporary location having a defined lifetime.

Clause 23. An apparatus to provide update data to a plurality of infusion pumps that are configured to deliver medication to one or more patients within a clinical environment, each infusion pump of the plurality of infusion pumps comprising memory configured to store operational software and one or more drug libraries, the apparatus comprising:

a processor comprising one or more hardware computers; and a memory storing instructions that, when executed by the processor, configure the apparatus to:

receive a first location of update data over a first communication channel of a first network that provides communication outside of the clinical environment;

receive the update data from the first location over a second communication channel of the first network; and store blocks of the update data at a second location that is within the clinical environment, wherein the stored blocks of update data are available for transmission to one or more infusion pumps of the plurality of infusion pumps over a second network within the clinical environment.

Clause 24. The apparatus of Clause 23 wherein the stored blocks of data are stored in cache memory.

Clause 25. The apparatus of Clause 23 wherein the update data is at least one of an operational software update and a drug library update.

Clause 26. A system configured to provide update data to a plurality of infusion pumps within a clinical environment, the system comprising:

a plurality of infusion pumps configured to deliver medication to one or more patients within a clinical environment, each infusion pump of the plurality of infusion pumps comprising memory configured to store operational software and one or more drug libraries; and an apparatus comprising computer hardware and memory configured to store at least the update data, the apparatus in communication with the plurality of infusion pumps over a first network that is within the clinical environment, the memory further storing instructions that, when executed by the computer hardware, configure the apparatus to:

receive the update data over a second network that provides communication outside of the clinical environment;

store the update data within the clinical environment as blocks of update data;

receive a request for the update data over a first communication channel of the first network from one or more infusion pumps of the plurality of infusion pumps; and stream the stored blocks of update data to a group of requesting infusion pumps over a second communication channel of the first network, wherein the group of requesting infusion pumps comprises a predetermined number of infusion pumps that is less than all of the plurality of infusion pumps, wherein the instructions further configure the apparatus to stream the stored blocks of update data to the group of requesting infusion pumps by streaming a first block of update data to a first subset of the group of requesting infusion pumps and approximately concurrently streaming a second block of update data different from the first block of update data to a second subset of the group of requesting infusion pumps.

Clause 27. The system of Clause 26 wherein the stored blocks of data are stored in cache memory.

Clause 28. The system of Clause 26 wherein the update data is at least one of an operational software update and a drug library update.

Clause 29. The system of Clause 26 wherein the apparatus is further configured to, in response to receiving the request for the update data, open a local URL stream.

Clause 30. The system of Clause 26 wherein the apparatus is further configured to notify the one or more infusion pumps that the update data is available.

Clause 31. The system of Clause 30 wherein the apparatus is further configured to determine the one or more infusion pumps based at least in part on filter information.

Clause 32. The system of Clause 31 wherein the filter information includes at least one of an indication of a specific infusion pump, an indication of a specific version of an infusion pump, or an indication of a specific facility.

Clause 33. The system of Clause 26 wherein said streaming the stored blocks of update data to the portion of requesting infusion pumps comprises staggering the streaming of blocks of update data to the portion of requesting infusion pumps.

Clause 34. The system of Clause 33 wherein staggering the streaming of blocks of update data to the portion of requesting infusion pumps comprises streaming blocks of update data in parallel to staggered groups of the portion of requesting infusion pumps.

Clause 35. The system of Clause 26 wherein the one or more infusion pumps are further configured to re-request the update data until the update data is sent, a frequency of re-requests occurring according to an exponential backoff process.

Clause 36. The system of Clause 26 wherein the one or more infusion pumps are configured to determine whether the memory associated with the respective infusion pump of the one or more infusion pumps includes the update data prior to requesting the update data.

Clause 37. A method to provide update data to a plurality of infusion pumps configured to deliver medication to one or more patients within a clinical environment, each infusion pump of the plurality of infusion pumps comprising memory configured to store operational software and one or more drug libraries, the method comprising:

receiving the update data over a second network that provides communication outside of the clinical environment;

storing the update data within the clinical environment as blocks of update data;

receiving a request for update data over a first communication channel of a first network from one or more infusion pumps of the plurality of infusion pumps, the first network being within the clinical environment; and staggering streaming of the stored blocks of update data to a group of requesting infusion pumps over a second communication channel of the first network, wherein the group of requesting infusion pumps comprises a predetermined number of infusion pumps that is less than all of the plurality of infusion pumps.

Clause 38. The method of Clause 37 wherein the stored blocks of data are stored in cache memory.

Clause 39. The system of Clause 37 wherein the update data is at least one of an operational software update and a drug library update.

Clause 40. An apparatus to provide update data to a plurality of infusion pumps configured to deliver medication to one or more patients within a clinical environment, each infusion pump of the plurality of infusion pumps comprising memory configured to store operational software and one or more drug libraries, the apparatus comprising:

a processor comprising one or more hardware computers; and a memory storing instructions that, when executed by the processor, configure the apparatus to:

receive the update data over a second network that provides communication outside of the clinical environment;

store the update data within the clinical environment as blocks of update data;

receive a request for update data over a first communication channel of a first network from one or more infusion pumps of the plurality of infusion pumps, the first network being within the clinical environment; and stagger streaming of the cached blocks of the update data to a group of requesting infusion pumps over a second communication channel of the first network, wherein the group of requesting infusion pumps comprises a predetermined number of infusion pumps that is less than all of the plurality of infusion pumps.

Clause 41. The apparatus of Clause 40 wherein the apparatus is further configured to, in response to receiving the request for the update data, open a local URL stream.

Clause 42. The apparatus of Clause 40 wherein the apparatus is further configured to notify the one or more infusion pumps that the update data is available.

Clause 43. The apparatus of Clause 42 wherein the apparatus is further configured to determine the one or more infusion pumps based at least in part on filter information.

Clause 44. The apparatus of Clause 43 wherein the filter information includes at least one of an indication of a specific infusion pump, an indication of a specific version of an infusion pump, or an indication of a specific facility.

Clause 45. An apparatus configured to receive operational software updates and drug library updates from a server and to communicate the operational software updates and drug library updates to a plurality of infusion pumps that deliver medication to one or more patients within a clinical environment, the apparatus further configured to determine communication performance quality of the apparatus, the apparatus comprising:

a processor comprising computing hardware; and a memory storing instructions that, when executed by the processor, configure the apparatus to:

monitor a plurality of parameters associated with one or more microservices, each microservice configured to determine functionality associated with operation of the apparatus, each parameter associated with a respective microservice;

determine that at least one parameter exceeds a threshold;

determine that messages transmitted to the server within a first time period exclude an indication that the at least one parameter exceeds the threshold;

format a message including an indication that the at least one parameter exceeds the threshold; and transmit the formatted message to the server and reset at least one respective microservice associated with the at least one parameter.

Clause 46. The apparatus of Clause 45 wherein the instructions further configure the apparatus to transmit the formatted message to the server only after a predetermined number parameters exceed their respective thresholds.

Clause 47. The apparatus of Clause 45 wherein the plurality of parameters include at least one of a queue size, latency, memory size, disk space, an indication of a number of connected devices, or CPU time.

Clause 48. The apparatus of Clause 45 wherein each microservice of the one or more microservices is configured to create containers of unstructured data associated with a monitored parameter of the plurality of parameters.

Clause 49. The apparatus of Clause 45 wherein the server is configured to receive a request from a user for a status of the apparatus.

Clause 50. The apparatus of Clause 45 wherein the server is configured to receive a request from a user for a status of the apparatus, and in response to receiving the request, transmit over the network to the apparatus, a request for status of at least one parameter of the plurality of parameters.

Clause 51. The apparatus of Clause 45 wherein the server is configured to receive and analyze the transmitted message.

Clause 52. The apparatus of Clause 51 wherein the server is further configured to report the analysis to a user.

Clause 53. The apparatus of Clause 51 wherein the server is further configured to automatically cause a reboot based on the analysis.

Clause 54. The apparatus of Clause 45 wherein the server is configured to cause the at least one respective microservice to reset.

Clause 55. A method to verify performance quality of an apparatus configured to communicate operational software updates and drug library updates from a server to a plurality of infusion pumps that deliver medication to one or more patients within a clinical environment, the method comprising:

monitoring a plurality of parameters associated with one or more microservices that monitor functionality associated with operation of the apparatus, each parameter associated with a respective microservice;

determining that at least one parameter exceeds a threshold; determining that messages transmitted to the server within a first time period exclude an indication that the at least one parameter exceeds the threshold;

formatting a message including an indication that the at least one parameter exceeds the threshold; and transmitting the formatted message to the server and reset at least one respective microservice associated with the at least one parameter.

Clause 56. The method of Clause 55 wherein the plurality of parameters include at least one of a queue size, latency, memory size, disk space, an indication of a number of connected devices, or CPU time.

Clause 57. The method of Clause 55 wherein each microservice of the one or more microservices is configured to create containers of unstructured data associated with a monitored parameter of the plurality of parameters.

Clause 58. The method of Clause 55 wherein the server is configured to receive a request from a user for a status of the apparatus.

Clause 59. The method of Clause 55 wherein the server is configured to receive a request from a user for a status of the apparatus, and in response to receiving the request, transmit over the network to the apparatus, a request for status of at least one parameter of the plurality of parameters.

Clause 60. The method of Clause 55 wherein the server is configured to receive and analyze the transmitted message.

Clause 61. The method of Clause 60 wherein the server is further configured to report the analysis to a user.

Clause 62. The method of Clause 60 wherein the server is further configured to automatically cause a reboot based on the analysis.

Clause 63. The method of Clause 55 wherein the server is configured to cause the at least one respective microservice to reset.

Clause 64. The method of Clause 55 wherein the apparatus is configured to cause the at least one respective microservice to reset.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A system configured to provide update data to a plurality of infusion pumps, the system comprising:
   a subset of infusion pumps of a plurality of infusion pumps, each infusion pump located within one or more clinical environments and configured to deliver medication according to operational software and one or more drug libraries to one or more patients;
   a server, located outside of the one or more clinical environments, configured to receive user input comprising a location of update data, the update data including one or more of updates to infusion pump operational software and updates to the one or more drug libraries; and
   a connectivity adapter comprising a first interface for communicating with the subset of infusion pumps over a first network that is within at least one of the one or more the clinical environments, the first interface configured to communicate messages over a first channel of the first network and communicate data over a second channel of the first network, and a second interface for communicating with the server over a second network that is outside of the one or more clinical environments and that is separate from the first network, the second interface configured to communicate messages over a first channel of the second network and communicate data over a second channel of the second network, the connectivity adapter further comprising computer hardware and memory having an outbound message queue and configured to store at least the update data, the memory further storing instructions that, when executed by the computer hardware, configure the connectivity adapter to:
   receive messages from the subset of infusion pumps over the first channel of the first network, the messages including clinical information;
   send transformed messages over the first channel of the second network to the server, the transformed messages based at least in part on the received messages that include the clinical information from the subset of infusion pumps;
   receive the update data from the server over the second channel of the second network that provides communication outside of the one or more clinical environments, wherein the second channel of the second network is separate from the first channel of the second network to prevent the receiving of the update data from interfering with the transformed messages that include the clinical information from the subset of infusion pumps;

store the update data within the memory of the connectivity adapter as blocks of update data;

receive a request for the update data over the first channel of the first network from one or more infusion pumps of the subset of infusion pumps;

determine a status of the first interface based on latency and size of the outbound message queue; and stream, based at least in part on the status, the stored blocks of update data to a group of requesting infusion pumps over the second channel of the first network, wherein the second channel of the first network is separate from the first channel of the first network to prevent the streaming of the stored blocks of update data to the group of requesting infusion pumps from interfering with the received messages that include the clinical information from the subset of infusion pumps, wherein the group of requesting infusion pumps comprises a predetermined number of infusion pumps that is less than all of the plurality of infusion pumps, wherein the instructions further configure the connectivity adapter to stream the stored blocks of update data to the group of requesting infusion pumps by streaming a first block of update data to a first subset of the group of requesting infusion pumps and approximately concurrently streaming a second block of update data different from the first block of update data to a second subset of the group of requesting infusion pumps.

2. The system of claim 1 wherein the stored blocks of data are stored in cache memory.

3. The system of claim 1 wherein the update data is at least one of an operational software update and a drug library update.

4. The system of claim 1, wherein the connectivity adapter is further configured to, in response to receiving the request for the update data, open a local URL stream.

5. The system of claim 1, wherein the connectivity adapter is further configured to notify the one or more infusion pumps that the update data is available.

6. The system of claim 5 wherein the connectivity adapter is further configured to determine the one or more infusion pumps based at least in part on filter information.

7. The system of claim 6 wherein the filter information includes at least one of an indication of a specific infusion pump, an indication of a specific version of an infusion pump, or an indication of a specific facility.

8. The system of claim 1 wherein said streaming the stored blocks of update data to the portion of requesting infusion pumps comprises staggering the streaming of blocks of update data to the portion of requesting infusion pumps.

9. The system of claim 8 wherein staggering the streaming of blocks of update data to the portion of requesting infusion pumps comprises streaming blocks of update data in parallel to staggered groups of the portion of requesting infusion pumps.

10. The system of claim 1 wherein the one or more infusion pumps are further configured to re-request the update data until the update data is sent, a frequency of re-requests occurring according to an exponential backoff process.

11. The system of claim 1 wherein the one or more infusion pumps are configured to determine whether the memory associated with the respective infusion pump of the one or more infusion pumps includes the update data prior to requesting the update data.

12. A method to provide update data to a plurality of infusion pumps configured to deliver medication according to operational software and one or more drug libraries to one or more patients, each infusion pump of the plurality of infusion pumps located within one or more clinical environments, the method comprising:

receiving, at a server, user input comprising a location of update data, the update data including one or more of updates to infusion pump operational software and updates to one or more drug libraries, the server located outside of one or more clinical environments;

receiving messages at a first interface of a connectivity adapter from a subset of the plurality of infusion pumps over a first channel of a first network, the messages including clinical information, the first network being within at least one of the one or more clinical environments, the first interface configured to communicate messages over the first channel of the first network and communicate data over a second channel of the first network, the connectivity message queue and configured to store at least the update data;

sending transformed messages to the server via a second interface of the connectivity adapter over a first channel of a second network, the second interface for communicating with the server over the second network that is outside of the one or more clinical environments and separate from the first network, the transformed messages based at least in part on the received messages that include the clinical information from the subset of infusion pumps, the second interface configured to communicate messages over the first channel of the second network and communicate data over a second channel of the second network;

receiving, with the connectivity adapter, the update data over the second channel of the second network that provides communication outside of the one or more clinical environments, wherein the second channel of the second network is separate from the first channel of the second network to prevent the receiving of the update data from interfering with the transformed messages that include the clinical information from the subset of infusion pumps;

storing, with the connectivity adapter, the update data within memory of the connectivity adapter as blocks of update data;

receiving, at the connectivity adapter, a request for the update data over the first channel of the first network from one or more infusion pumps of the subset of infusion pumps, the first network being within the one or more clinical environments;

determine a status of the first interface based on latency and size of the outbound message queue; and staggering, with the connectivity adapter, based at least in part on the status, a streaming of the stored blocks of update data to a group of requesting infusion pumps over a second channel of the first network, wherein the second channel of the first network is separate from the first channel of the first network to prevent the streaming of the stored blocks of update data to the group of requesting infusion pumps from interfering with the received messages that include the clinical information from the subset of infusion pumps, wherein the group of requesting infusion pumps comprises a predetermined number of infusion pumps that is less than all of the subset of infusion pumps.

13. The method of claim 12 wherein the stored blocks of data are stored in cache memory.

14. The method of claim 12 wherein the update data is at least one of an operational software update and a drug library update.

15. An apparatus to provide update data to a plurality of infusion pumps configured to deliver medication according to operational software and one or more drug libraries to one or more patients, each infusion pump of the plurality of infusion pumps located within one or more clinical environments, the apparatus comprising:
   a first interface configured to communicate with the plurality of infusion pumps over a first network that is within at least one of the one or more clinical environments, the first interface configured to communicate messages over a first channel of the first network and communicate data over a second channel of the first network;
   a second interface configured to communicate to a server over a second network that is outside of the one or more clinical environments and separate from the first network, the second interface configured to communicate messages over a first channel of the second network and communicate data over a second channel of the second network;
   a processor comprising one or more hardware computers; and
   a memory having an outbound message queue storing instructions that; when executed by the processor, configure the apparatus to:
      receive messages at the first interface from a subset of the plurality of infusion pumps over the first channel of the first network, the messages including clinical information;
      send transformed messages to the server via the second interface over the first channel of the second network, the transformed messages based at least in part on the received messages that include the clinical information from the subset of infusion pumps;
      receive the update data from the server over a second channel of the second network that provides communication outside of the one or more clinical environments, the server configured to receive user input comprising a location of the update data, the update data including one or more of updates to infusion pump operational software and updates to one or more drug libraries, wherein the second channel of the second network is separate from the first channel of the second network to prevent the receiving of the update data from interfering with the transformed messages that include the clinical information from the subset of infusion pumps;
      store the update data within the memory as blocks of update data;
      receive a request for update data over the first channel of the first network from one or more infusion pumps of the subset of infusion pumps;
      determine a status of the first interface based on latency and size of the outbound message queue; and
      stagger, based at least in part on the status, a streaming of the cached blocks of the update data to a group of requesting infusion pumps over the second channel of the first network, wherein the second channel of the first network is separate from the first channel of the first network to prevent the streaming of the stored blocks of update data to the group of requesting infusion pumps from interfering with the received messages that include the clinical information from the subset of infusion pumps, wherein the group of requesting infusion pumps comprises a predetermined number of infusion pumps that is less than all of the subset of infusion pumps.

16. The apparatus of claim 15 wherein the apparatus is further configured to, in response to receiving the request for the update data, open a local URL stream.

17. The apparatus of claim 15 wherein the apparatus is further configured to notify the one or more infusion pumps that the update data is available.

18. The apparatus of claim 17 wherein the apparatus is further configured to determine the one or more infusion pumps based at least in part on filter information.

19. The apparatus of claim 18 wherein the filter information includes at least one of an indication of a specific infusion pump, an indication of a specific version of an infusion pump, or an indication of a specific facility.

* * * * *

UNITED STATES PATENT AND TRADEMARK OFFICE
CERTIFICATE OF CORRECTION

PATENT NO. : 10,861,592 B2
APPLICATION NO. : 16/512193
DATED : December 8, 2020
INVENTOR(S) : Ben Xavier et al.

It is certified that error appears in the above-identified patent and that said Letters Patent is hereby corrected as shown below:

On the Title Page

On page 10, in Column 2, item (56), OTHER PUBLICATIONS, Line 34, delete "Computing13" and insert --Computing- --.

On page 10, in Column 2, item (56), OTHER PUBLICATIONS, Line 54, delete "Verification"" and insert --Verification",--.

On page 10, in Column 2, item (56), OTHER PUBLICATIONS, Line 54, delete "org" and insert --org,--.

On page 10, in Column 2, item (56), OTHER PUBLICATIONS, Line 54, delete "11" and insert --11,--.

In the Specification

In Column 21, Line 59, delete "environment;" and insert --environment.--.

In the Claims

In Column 31, Line 40, Claim 4, delete "1," and insert --1--.

In Column 31, Line 43, Claim 5, delete "1," and insert --1--.

In Column 32, Line 25, Claim 12, after "connectivity" insert --adapter further comprising computer hardware and memory having an outbound--.

In Column 33, Line 31, Claim 15, delete "queue" and insert --queue and--.

In Column 33, Line 32, Claim 15, delete "that;" and insert --that,--.

Signed and Sealed this
Second Day of March, 2021

Drew Hirshfeld
*Performing the Functions and Duties of the
Under Secretary of Commerce for Intellectual Property and
Director of the United States Patent and Trademark Office*